United States Patent [19]
Gunn et al.

[11] Patent Number: 6,110,695
[45] Date of Patent: Aug. 29, 2000

[54] MODULATING THE INTERACTION OF THE CHEMOKINE, B LYMPHOCYTE HEMOATTRACTANT, AND ITS RECEPTOR, BLR1

[75] Inventors: Michael Dee Gunn, San Francisco; Lewis T. Williams, Tiburon; Jason G. Cyster, San Francisco, all of Calif.

[73] Assignee: The Regents of the University of California, Oakland, Calif.

[21] Appl. No.: 08/982,493

[22] Filed: Dec. 2, 1997

[51] Int. Cl.[7] .......................... G01N 33/50; A61K 38/19
[52] U.S. Cl. .......................... 435/7.24; 435/7.1; 435/7.2; 435/7.21; 435/29; 424/85.1
[58] Field of Search ................. 424/85.1; 435/7.1, 435/7.2, 7.21, 7.24, 29

[56] References Cited

U.S. PATENT DOCUMENTS

| | | | |
|---|---|---|---|
| 5,844,084 | 12/1998 | Guegler et al. | 530/351 |
| 5,919,896 | 7/1999 | Lee et al. | 530/324 |

FOREIGN PATENT DOCUMENTS

| | | |
|---|---|---|
| 9202639 | 2/1992 | WIPO . |
| 9508001 | 3/1995 | WIPO . |
| 9528482 | 10/1995 | WIPO . |
| 9622371 | 7/1996 | WIPO . |
| 9624668 | 8/1996 | WIPO . |

OTHER PUBLICATIONS

WO 96 39522 A (Human Genome Sciences Inc; Li Haodong (US)) Dec. 12, 1996. See abstract. See p. 1, paragraph 2–p. 2, pargraph 3. See p. 24, paragraph 3–p. 25, paragraph 3. See examples 2,4,6. See claims 1–20. Seq. ID 4.

Förster, R., et al. (1986). A putative chemokine receptor, BLR1, directs B cell migration to defined lymphoid organs and specific anatomic compartments of the spleen. *Cell* 87: 1037–47, Dec. 1996.

Legler, D.F., et al. (1998). B cell–attracting chemokine 1, a human CXC chemokine expressed in lymphoid tissues, selectively attracts B lymphocytes via BLR1/CXCR5. *J. Exp. Med.* 187: 655–60, Feb. 1998.

Howard et al, *TTBTECH* 14, Feb. 1996, p. 46–51.

Hodgson, *Bio/Technol* 10, Sep. 1992, p. 973–77.

Wells et al, *J. Leukocyte Biol.* 59, Jan. 1996.

*Primary Examiner*—David L. Fitzgerald
*Attorney, Agent, or Firm*—Richard Aron Osman

[57] ABSTRACT

The invention provides methods for identifying agents which modulate the interaction of a chemokine receptor of previously unknown function, Burkitt's Lymphoma Receptor 1 (BLR1), with its ligand, B Lymphocyte Chemoattractant (BLC). The methods find particular application in commercial drug screens.

33 Claims, 6 Drawing Sheets

- ● BLC
- □ SDF1α
- ▽ IL-8

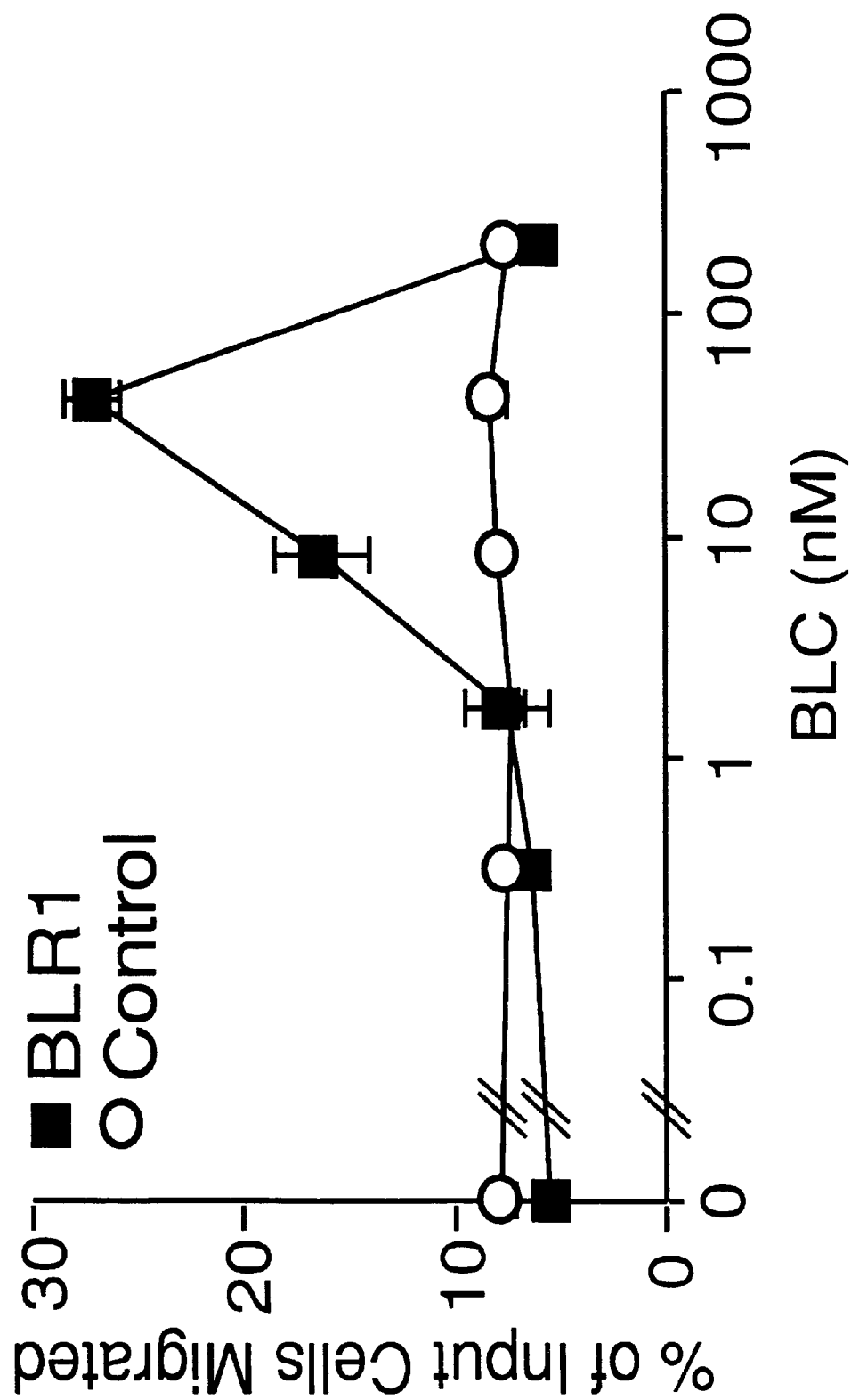

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1181 base pairs
      (B) TYPE: nucleic acid
      (C) STRANDEDNESS: double
      (D) TOPOLOGY: linear (ii) MOLECULE TYPE: cDNA (ix) FEATURE:
    (A) NAME/KEY: CDS
    (B) LOCATION: 33..359

(xi) SEQUENCE DESCRIPTION: SEQ ID NO:1:

```
GAGCTAAAGG TTGAACTCCA CCTCCAGGCA GA ATG AGG CTC AGC ACA GCA ACG         53
                                   Met Arg Leu Ser Thr Ala Thr
                                    1               5

CTG CTT CTC CTC CTG GCC AGC TGC CTC TCT CCA GGC CAC GGT ATT CTG        101
Leu Leu Leu Leu Leu Ala Ser Cys Leu Ser Pro Gly His Gly Ile Leu
            10                  15                  20

GAA GCC CAT TAC ACA AAC TTA AAA TGT AGG TGT TCT GGA GTG ATT TCA        149
Glu Ala His Tyr Thr Asn Leu Lys Cys Arg Cys Ser Gly Val Ile Ser
 25                  30                  35

ACT GTT GTC GGT CTA AAC ATC ATA GAT CGG ATT CAA GTT ACG CCC CCT        197
Thr Val Val Gly Leu Asn Ile Ile Asp Arg Ile Gln Val Thr Pro Pro
 40                  45                  50                  55

GGG AAT GGC TGC CCC AAA ACT GAA GTT GTG ATC TGG ACC AAG ATG AAG        245
Gly Asn Gly Cys Pro Lys Thr Glu Val Val Ile Trp Thr Lys Met Lys
                 60                  65                  70

AAA GTT ATA TGT GTG AAT CCT CGT GCC AAA TGG TTA CAA AGA TTA TTA        293
Lys Val Ile Cys Val Asn Pro Arg Ala Lys Trp Leu Gln Arg Leu Leu
             75                  80                  85

AGA CAT GTC CAA AGC AAA AGT CTG TCT TCA ACT CCC CAA GCT CCA GTG        341
Arg His Val Gln Ser Lys Ser Leu Ser Ser Thr Pro Gln Ala Pro Val
             90                  95                 100

AGT AAG AGA AGA GCT GCC TGAAGCCACT ATCATCTCAA AAGACACACC               389
Ser Lys Arg Arg Ala Ala
            105

TGCACCTTTT TTTTTATCCC TGCTCTGAAT TTTAGATATG TTCTTAGTTA AAGAATTTCC      449

AAGAAAATAA CTCCCCTCTA CAAACAAACA TGACTGTAGG TAAAACAAAG CAAAACAAA       509

CAAGCAAACA AACAAACTAA AAAAAACCCA ATCCTGCAGG AGCTGAGAGG GAATGCTCAA      569

GCTCCGTTGC ATACCCAACC CACATCCTTG TTCCTTAAGA AAGGCTATTT GAGAACAGGC      629

ATTTAGTGAC AACCCACTTC AGATGCATGT GGTAATAGAT CTGTTGTTTA ATGTTAAACT      689

ATCCTAGATT GTCGAGGAAT GAAAAACCTA CATGTCAAAT GTGAACTTGT AGCTCGTACT      749

AACAAGAGGT TTGCGAGATG GACTTCAGTT ATTTTGCACC CTTGTAAAAC GCAGGCTTCC      809

AAAATAGTCT CCAGAAGGTT CCTGGGAAGC TGGTGCAATG CCATCATGAG GTGGTGCAAA      869

GCAGGTCTCC TTTAGAGAAA AGCTTCCTGG GGGAAACAGT CCTACTTTGA AAGGTTGCTT      929

GTATAAGATT TATTGTCTTG CATTAAAACC AGTAACAATT GAAAGATCCT CAGCTTAAAG      989

GTCCAGGCTC TTCAGCAGTA TACAAATATA TTCCTTTGCA CTGTGACCCT GATGATCTAT     1049

TTTTATTATT CATATTTTTC ACACAGACAA AATACCAGCC TCTTGTATCA GATTCTTTAA     1109

TGTTTCCTAT TCATTTGGTG TCATTCAATA AATGTAATCA AATGTTTTGC TTAAAAAAAA     1169

AAAAAAAAAA AA                                                        1181
```

(2) INFORMATION FOR SEQ ID NO:2:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Leu Ser Thr Ala Thr Leu Leu Leu Leu Ala Ser Cys Leu
  1               5                  10                 15

Ser Pro Gly His Gly Ile Leu Glu Ala His Tyr Thr Asn Leu Lys Cys
             20                  25                 30

Arg Cys Ser Gly Val Ile Ser Thr Val Val Gly Leu Asn Ile Ile Asp
         35                  40                  45

Arg Ile Gln Val Thr Pro Pro Gly Asn Gly Cys Pro Lys Thr Glu Val
 50                  55                  60

Val Ile Trp Thr Lys Met Lys Lys Val Ile Cys Val Asn Pro Arg Ala
 65                  70                  75                  80

Lys Trp Leu Gln Arg Leu Leu Arg His Val Gln Ser Lys Ser Leu Ser
             85                  90                  95

Ser Thr Pro Gln Ala Pro Val Ser Lys Arg Arg Ala Ala
            100                 105
```

(2) INFORMATION FOR SEQ ID NO:3:

(i) SEQUENCE CHARACTERISTICS:
        (A) LENGTH: 1228 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 91..417

(xi) SEQUENCE DESCRIPTION: SEQ ID NO:3:

```
TTCGGCACTT GGGAGAAGAT GTTTGAAAAA ACTGACTCTG CTAATGAGCC TGGACTCAGA      60

GCTCAAGTCT GAACTCTACC TCCAGACAGA ATG AAG TTC ATC TCG ACA TCT CTG     114
                                Met Lys Phe Ile Ser Thr Ser Leu
                                    110                 115

CTT CTC ATG CTG CTG GTC AGC AGC CTC TCT CCA GTC CAA GGT GTT CTG     162
Leu Leu Met Leu Leu Val Ser Ser Leu Ser Pro Val Gln Gly Val Leu
        120                 125                 130

GAG GTC TAT TAC ACA AGC TTG AGG TGT AGA TGT GTC CAA GAG AGC TCA     210
Glu Val Tyr Tyr Thr Ser Leu Arg Cys Arg Cys Val Gln Glu Ser Ser
135                 140                 145

GTC TTT ATC CCT AGA CGC TTC ATT GAT CGA ATT CAA ATC TTG CCC CGT     258
Val Phe Ile Pro Arg Arg Phe Ile Asp Arg Ile Gln Ile Leu Pro Arg
150                 155                 160                 165

GGG AAT GGT TGT CCA AGA AAA GAA ATC ATA GTC TGG AAG AAG AAC AAG     306
Gly Asn Gly Cys Pro Arg Lys Glu Ile Ile Val Trp Lys Lys Asn Lys
                170                 175                 180

TCA ATT GTG TGT GTG GAC CCT CAA GCT GAA TGG ATA CAA AGA ATG ATG     354
Ser Ile Val Cys Val Asp Pro Gln Ala Glu Trp Ile Gln Arg Met Met
            185                 190                 195

GAA GTA TTG AGA AAA AGA AGT TCT TCA ACT CTA CCA GTT CCA GTG TTT     402
Glu Val Leu Arg Lys Arg Ser Ser Ser Thr Leu Pro Val Pro Val Phe
        200                 205                 210

AAG AGA AAG ATT CCC TGATGCTGAT ATTTCCACTA AGAACACCTG CATTCTTCCC     457
Lys Arg Lys Ile Pro
        215

TTATCCCTGC TCTGGATTTT AGTTTTGTGC TTAGTTAAAT CTTTTCCAGG GAGAAAGAAC     517

TTCCCCATAC AAATAAGGCA TGAGGACTAT GTGAAAAATA ACCTTGCAGG AGCTGATGGG     577

GCAAACTCAA GCTTCTTCAC TCACAGCACC CTATATACAC TTGGAGTTTG CATTCTTATT     637

CATCAGGGAG GAAAGTTTCT TTGAAAATAG TTATTCAGTT ATAAGTAATA CAGGATTATT     697
```

```
TTGATTATAT ACTTGTTGTT TAATGTTTAA AATTTCTTAG AAAACAATGG AATGAGAATT      757

TAAGCCTCAA ATTTGAACAT GTGGCTTGAA TTAAGAAGAA AATTATGGCA TATATTAAAA      817

GCAGGCTTCT ATGAAAGACT CAAAAAGCTG CCTGGGAGGC AGATGGAACT TGAGCCTGTC      877

AAGAGGCAAA GGAATCCATG TAGTAGATAT CCTCTGCTTA AAAACTCACT ACGGAGGAGA      937

ATTAAGTCCT ACTTTTAAAG AATTTCTTTA TAAAATTTAC TGTCTAAGAT TAATAGCATT      997

CGAAGATCCC CAGACTTCAT AGAATACTCA GGGAAAGCAT TTAAAGGGTG ATGTACACAT     1057

GTATCCTTTC ACACATTTGC CTTGACAAAC TTCTTTCACT CACATCTTTT TCACTGACTT     1117

TTTTTGTGGG GGCGGGGCCG GGGGGACTCT GGTATCTAAT TCTTTAATGA TTCCTATAAA     1177

TCTAATGACA TTCAATAAAG TTGAGCAAAC ATTTTACTTA AAAAAAAAA A              1228
```

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Phe Ile Ser Thr Ser Leu Leu Leu Met Leu Leu Val Ser Ser
  1               5                  10                  15

Leu Ser Pro Val Gln Gly Val Leu Glu Val Tyr Tyr Thr Ser Leu Arg
             20                  25                  30

Cys Arg Cys Val Gln Glu Ser Ser Val Phe Ile Pro Arg Arg Phe Ile
         35                  40                  45

Asp Arg Ile Gln Ile Leu Pro Arg Gly Asn Gly Cys Pro Arg Lys Glu
     50                  55                  60

Ile Ile Val Trp Lys Lys Asn Lys Ser Ile Val Cys Val Asp Pro Gln
 65                  70                  75                  80

Ala Glu Trp Ile Gln Arg Met Met Glu Val Leu Arg Lys Arg Ser Ser
                 85                  90                  95

Ser Thr Leu Pro Val Pro Val Phe Lys Arg Lys Ile Pro
                100                 105
```

(2) INFORMATION FOR SEQ ID NO:5:

(i) SEQUENCE CHARACTERISTICS:
        (A) LENGTH: 2517 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1122

(xi) SEQUENCE DESCRIPTION: SEQ ID NO:5:

```
ATG AAC TAC CCA CTA ACC CTG GAC ATG GGC TCC ATC ACA TAC AAT ATG        48
Met Asn Tyr Pro Leu Thr Leu Asp Met Gly Ser Ile Thr Tyr Asn Met
110                 115                 120                 125

GAT GAC CTG TAC AAG GAA CTG GCC TTC TAC AGT AAC AGC ACG GAG ATT        96
Asp Asp Leu Tyr Lys Glu Leu Ala Phe Tyr Ser Asn Ser Thr Glu Ile
                130                 135                 140

CCC CTA CAG GAC AGT AAC TTC TGC TCT ACA GTC GAG GGA CCC TTA CTG       144
Pro Leu Gln Asp Ser Asn Phe Cys Ser Thr Val Glu Gly Pro Leu Leu
```

-continued

|  |  |  |
|---|---|---|
| ACG TCC TTT AAG GCG GTA TTC ATG CCT GTG GCC TAC AGC CTC ATC TTC<br>Thr Ser Phe Lys Ala Val Phe Met Pro Val Ala Tyr Ser Leu Ile Phe<br>160 165 170 | 192 |
| CTC CTG GGT ATG ATG GGA AAC ATC CTG GTG CTG GTA ATC CTG GAG AGG<br>Leu Leu Gly Met Met Gly Asn Ile Leu Val Leu Val Ile Leu Glu Arg<br>175 180 185 | 240 |
| CAC CGG CAC ACT CGG AGC TCA ACC GAG ACC TTC CTG TTC CAC CTC GCA<br>His Arg His Thr Arg Ser Ser Thr Glu Thr Phe Leu Phe His Leu Ala<br>190 195 200 205 | 288 |
| GTA GCC GAC CTT CTC TTA GTC TTC ATC CTG CCT TTT GCA GTG GCT GAG<br>Val Ala Asp Leu Leu Leu Val Phe Ile Leu Pro Phe Ala Val Ala Glu<br>210 215 220 | 336 |
| GGC TCT GTG GGT TGG GTC CTA GGG ACC TTC CTC TGC AAA ACT GTG ATC<br>Gly Ser Val Gly Trp Val Leu Gly Thr Phe Leu Cys Lys Thr Val Ile<br>225 230 235 | 384 |
| GCT CTG CAC AAG ATC AAT TTC TAC TGC AGC AGC CTC CTC GTG GCC TGT<br>Ala Leu His Lys Ile Asn Phe Tyr Cys Ser Ser Leu Leu Val Ala Cys<br>240 245 250 | 432 |
| ATA GCT GTA GAC CGG TAC CTA GCC ATC GTC CAT GCT GTT CAC GCC TAC<br>Ile Ala Val Asp Arg Tyr Leu Ala Ile Val His Ala Val His Ala Tyr<br>255 260 265 | 480 |
| CGC CGC CGT CGA CTC CTC TCC ATC CAC ATC ACC TGC ACG GCC ATT TGG<br>Arg Arg Arg Arg Leu Leu Ser Ile His Ile Thr Cys Thr Ala Ile Trp<br>270 275 280 285 | 528 |
| CTG GCC GGC TTC CTG TTC GCC TTA CCG GAA CTC CTC TTT GCC AAG GTT<br>Leu Ala Gly Phe Leu Phe Ala Leu Pro Glu Leu Leu Phe Ala Lys Val<br>290 295 300 | 576 |
| GGC CAA CCT CAT AAC AAC GAC TCC TTA CCA CAG TGC ACC TTC TCC CAG<br>Gly Gln Pro His Asn Asn Asp Ser Leu Pro Gln Cys Thr Phe Ser Gln<br>305 310 315 | 624 |
| GAA AAC GAA GCG GAA ACT AGA GCC TGG TTC ACC TCC CGT TTC CTC TAC<br>Glu Asn Glu Ala Glu Thr Arg Ala Trp Phe Thr Ser Arg Phe Leu Tyr<br>320 325 330 | 672 |
| CAC ATC GGG GGC TTC CTA CTA CCG ATG CTT GTG ATG GGA TGG TGT TAC<br>His Ile Gly Gly Phe Leu Leu Pro Met Leu Val Met Gly Trp Cys Tyr<br>335 340 345 | 720 |
| GTG GGC GTG GTC CAC AGG CTA CTG CAG GCC CAG CGG CGC CCT CAG CGG<br>Val Gly Val Val His Arg Leu Leu Gln Ala Gln Arg Arg Pro Gln Arg<br>350 355 360 365 | 768 |
| CAG AAG GCG GTC AGG GTG GCC ATT TTA GTG ACA AGC ATT TTC TTC CTC<br>Gln Lys Ala Val Arg Val Ala Ile Leu Val Thr Ser Ile Phe Phe Leu<br>370 375 380 | 816 |
| TGC TGG TCG CCC TAC CAC ATT GTC ATC TTC CTA GAT ACA CTG GAG AGG<br>Cys Trp Ser Pro Tyr His Ile Val Ile Phe Leu Asp Thr Leu Glu Arg<br>385 390 395 | 864 |
| CTG AAG GCT GTG AAT AGC AGC TGC GAG CTG AGT GGC TAT CTC TCT GTG<br>Leu Lys Ala Val Asn Ser Ser Cys Glu Leu Ser Gly Tyr Leu Ser Val<br>400 405 410 | 912 |
| GCC ATC ACC TTG TGT GAA TTC CTG GGC CTG GCA CAC TGC TGT CTC AAT<br>Ala Ile Thr Leu Cys Glu Phe Leu Gly Leu Ala His Cys Cys Leu Asn<br>415 420 425 | 960 |
| CCC ATG CTT TAC ACC TTC GCT GGC GTA AAG TTC CGC AGT GAC CTC TCT<br>Pro Met Leu Tyr Thr Phe Ala Gly Val Lys Phe Arg Ser Asp Leu Ser<br>430 435 440 445 | 1008 |
| CGG CTT CTG ACC AAG CTG GGC TGT GCT GGC CCG GCC TCC CTT TGC CAA<br>Arg Leu Leu Thr Lys Leu Gly Cys Ala Gly Pro Ala Ser Leu Cys Gln<br>450 455 460 | 1056 |
| CTT TTC CCC AAC TGG CGC AAG AGT AGT CTC TCT GAG TCA GAG AAT GCT | 1104 |

```
Leu Phe Pro Asn Trp Arg Lys Ser Ser Leu Ser Glu Ser Glu Asn Ala
            465                 470                 475
ACT TCC CTC ACC ACC TTC TAGATCCCGG AAGTCTCGGG GCCCCTGTCT           1152
Thr Ser Leu Thr Thr Phe
            480

GTTTCTGTTT TCCTTGGGAG GATAAAGTGG TGGCGGAACC CATCCAACTC GAGCTTGGGC  1212

CAGTGTCCCC AGATGGGAAA GCTAGATAAA CTCTCTCAAA CTTTCCCAAA GGGGAAAGCA  1272

GCCCAAAGGC AAAGCAAGCT ATATCCAGGC CACCTGTATC ACCTTAGATG AAGAGAACTC  1332

CATACACCTC CCATCCTAAC CAGCTAAAGC TAAGCTCAGC TTTATTTCTT CCTGGCCATA  1392

GGGACAACCA CCTCTGCTGT GGCCCACAGT CTCATCTTCC TCCTGATTAT GAGCCCAGAC  1452

TCTCCTCCCA GAATGTATTC CATCATCTTA AAGACTACTG GCTGCCACAG CTACCCACCA  1512

CTCCTATACC ACAGAGGAAT AGCCAGGCTG GGCGGCGGCA GACTATGGCC TTAATGTGCC  1572

TGTCTCATAA ATACAGACTT CATGCCAGAC CTTCAACCGT GCCTTTCTCT TAACCAAGCA  1632

GAAAGCTGAA ACCGATCTAC TTTAGGTAGC TGTCTGGTTC CAACCTAACC AGCATTGGGT  1692

CAGCCCCATG TTACTGGATC TTGGATTACA GACTGAGGGC AAGTTCCAGA AGGTTCTGGA  1752

AGCTAGCCAG TATCCTAAGA AGAGTAAAGG GCAAGCCAGC AGGAAAGAGG CCCAGTGGAA  1812

AAGTGGAAAG ACACCTTTTC CAGGCTCTAA GGAAGAACAA GTAAAAATCA AACCCAGCTG  1872

TCTTCTCCAC CCAATGTACC AAAGCTTACA GACTGGTGGG GAAATGAGAT CCAGGGCCCT  1932

CGTGGATTCT ACGCACCAAT GGGGAAGGAA GCCAACTTGC CTGGGGAAAG CAAGATAGCA  1992

AAGTGGTCCT AGCCTCGAGA GAGGGACACC TAGCTAAGAG AATGACGACA GAGGTTCCTG  2052

TCTTCATTAG GCAGAGGCAA TATAAGAAGC CAACCTGGGC AGGCAAGTCC TCAAACCCCA  2112

GGAAGCAGTA CCCTGCCCCT GGGAGGGTAC CACTCACATG GAACCAGAGG AAGCTGCTCC  2172

ATGCATACAT AGGGGAAGTT AGCAGGCAAT TCTGAGCTCG GCTTCCTCCC AGCCACCGAT  2232

CTGGGGGCGT GGGGGTAGGA AGCAGAGTTG CCTAGTACAC TCAAGCCAAC CGTACAAGCT  2292

CCCTGGGGGA TCCCACTGGG GAAACCAATG CTATAGCTTC AGAGACTGTA TCCTCATTGC  2352

AGAACCGTGA AGACACCTGG GGACCCCCTT TTCTGCTCCC AGCATCCAAC AACCAGCTGG  2412

GAAGAGGCAA ACCGGGCACA GAAATAAAAA TGCAAGAGAT GGCATTTTTG AATTTTCTCT  2472

TTTTAATAAA AAGGCACCTA TAAAACAGGT CAATACAGGC AGAGA                 2517

(2) INFORMATION FOR SEQ ID NO:6:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Tyr Pro Leu Thr Leu Asp Met Gly Ser Ile Thr Tyr Asn Met
 1               5                  10                  15

Asp Asp Leu Tyr Lys Glu Leu Ala Phe Tyr Ser Asn Ser Thr Glu Ile
            20                  25                  30

Pro Leu Gln Asp Ser Asn Phe Cys Ser Thr Val Glu Gly Pro Leu Leu
        35                  40                  45

Thr Ser Phe Lys Ala Val Phe Met Pro Val Ala Tyr Ser Leu Ile Phe
    50                  55                  60

Leu Leu Gly Met Met Gly Asn Ile Leu Val Leu Val Ile Leu Glu Arg
65                  70                  75                  80
```

His Arg His Thr Arg Ser Ser Thr Glu Thr Phe Leu Phe His Leu Ala
                85                  90                  95

Val Ala Asp Leu Leu Leu Val Phe Ile Leu Pro Phe Ala Val Ala Glu
            100                 105                 110

Gly Ser Val Gly Trp Val Leu Gly Thr Phe Leu Cys Lys Thr Val Ile
            115                 120                 125

Ala Leu His Lys Ile Asn Phe Tyr Cys Ser Ser Leu Leu Val Ala Cys
    130                 135                 140

Ile Ala Val Asp Arg Tyr Leu Ala Ile Val His Ala Val His Ala Tyr
145                 150                 155                 160

Arg Arg Arg Arg Leu Leu Ser Ile His Ile Thr Cys Thr Ala Ile Trp
                165                 170                 175

Leu Ala Gly Phe Leu Phe Ala Leu Pro Glu Leu Leu Phe Ala Lys Val
            180                 185                 190

Gly Gln Pro His Asn Asn Asp Ser Leu Pro Gln Cys Thr Phe Ser Gln
            195                 200                 205

Glu Asn Glu Ala Glu Thr Arg Ala Trp Phe Thr Ser Arg Phe Leu Tyr
    210                 215                 220

His Ile Gly Gly Phe Leu Leu Pro Met Leu Val Met Gly Trp Cys Tyr
225                 230                 235                 240

Val Gly Val Val His Arg Leu Leu Gln Ala Gln Arg Arg Pro Gln Arg
                245                 250                 255

Gln Lys Ala Val Arg Val Ala Ile Leu Val Thr Ser Ile Phe Phe Leu
            260                 265                 270

Cys Trp Ser Pro Tyr His Ile Val Ile Phe Leu Asp Thr Leu Glu Arg
            275                 280                 285

Leu Lys Ala Val Asn Ser Ser Cys Glu Leu Ser Gly Tyr Leu Ser Val
    290                 295                 300

Ala Ile Thr Leu Cys Glu Phe Leu Gly Leu Ala His Cys Cys Leu Asn
305                 310                 315                 320

Pro Met Leu Tyr Thr Phe Ala Gly Val Lys Phe Arg Ser Asp Leu Ser
                325                 330                 335

Arg Leu Leu Thr Lys Leu Gly Cys Ala Gly Pro Ala Ser Leu Cys Gln
            340                 345                 350

Leu Phe Pro Asn Trp Arg Lys Ser Ser Leu Ser Glu Ser Glu Asn Ala
            355                 360                 365

Thr Ser Leu Thr Thr Phe
    370

(2) INFORMATION FOR SEQ ID NO:7:

(i) SEQUENCE CHARACTERISTICS:
        (A) LENGTH: 2818 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 85..1200

(xi) SEQUENCE DESCRIPTION: SEQ ID NO:7:

```
GCTGCCACCT CTCTAGAGGC ACCTGGCGGG GAGCCTCTCA ACATAAGACA GTGACCAGTC      60

TGGTGACTCA CAGCCGGCAC AGCC ATG AAC TAC CCG CTA ACG CTG GAA ATG       111
                          Met Asn Tyr Pro Leu Thr Leu Glu Met
```

-continued

```
                        375                     380
GAC CTC GAG AAC CTG GAG GAC CTG TTC TGG GAA CTG GAC AGA TTG GAC         159
Asp Leu Glu Asn Leu Glu Asp Leu Phe Trp Glu Leu Asp Arg Leu Asp
385                     390                     395

AAC TAT AAC GAC ACC TCC CTG GTG GAA AAT CAT CTC TGC CCT GCC ACA         207
Asn Tyr Asn Asp Thr Ser Leu Val Glu Asn His Leu Cys Pro Ala Thr
400                     405                     410                 415

GAG GGT CCC CTC ATG GCC TCC TTC AAG GCC GTG TTC GTG CCC GTG GCC         255
Glu Gly Pro Leu Met Ala Ser Phe Lys Ala Val Phe Val Pro Val Ala
                    420                     425                 430

TAC AGC CTC ATC TTC CTC CTG GGC GTG ATC GGC AAC GTC CTG GTG CTG         303
Tyr Ser Leu Ile Phe Leu Leu Gly Val Ile Gly Asn Val Leu Val Leu
                435                     440                 445

GTG ATC CTG GAG CGG CAC CGG CAG ACA CGC AGT TCC ACG GAG ACC TTC         351
Val Ile Leu Glu Arg His Arg Gln Thr Arg Ser Ser Thr Glu Thr Phe
            450                     455                 460

CTG TTC CAC CTG GCC GTG GCC GAC CTC CTG CTG GTC TTC ATC TTG CCC         399
Leu Phe His Leu Ala Val Ala Asp Leu Leu Leu Val Phe Ile Leu Pro
        465                     470                 475

TTT GCC GTG GCC GAG GGC TCT GTG GGC TGG GTC CTG GGG ACC TTC CTC         447
Phe Ala Val Ala Glu Gly Ser Val Gly Trp Val Leu Gly Thr Phe Leu
480                     485                     490                 495

TGC AAA ACT GTG ATT GCC CTG CAC AAA GTC AAC TTC TAC TGC AGC AGC         495
Cys Lys Thr Val Ile Ala Leu His Lys Val Asn Phe Tyr Cys Ser Ser
                    500                     505                 510

CTG CTC CTG GCC TGC ATC GCC GTG GAC CGC TAC CTG GCC ATT GTC CAC         543
Leu Leu Leu Ala Cys Ile Ala Val Asp Arg Tyr Leu Ala Ile Val His
                515                     520                 525

GCC GTC CAT GCC TAC CGC CAC CGC CGC CTC CTC TCC ATC CAC ATC ACC         591
Ala Val His Ala Tyr Arg His Arg Arg Leu Leu Ser Ile His Ile Thr
            530                     535                 540

TGT GGG ACC ATC TGG CTG GTG GGC TTC CTC CTT GCC TTG CCA GAG ATT         639
Cys Gly Thr Ile Trp Leu Val Gly Phe Leu Leu Ala Leu Pro Glu Ile
        545                     550                 555

CTC TTC GCC AAA GTC AGC CAA GGC CAT CAC AAC AAC TCC CTG CCA CGT         687
Leu Phe Ala Lys Val Ser Gln Gly His His Asn Asn Ser Leu Pro Arg
560                     565                     570                 575

TGC ACC TTC TCC CAA GAG AAC CAA GCA GAA ACG CAT GCC TGG TTC ACC         735
Cys Thr Phe Ser Gln Glu Asn Gln Ala Glu Thr His Ala Trp Phe Thr
                    580                     585                 590

TCC CGA TTC CTC TAC CAT GTG GCG GGA TTC CTG CTG CCC ATG CTG GTG         783
Ser Arg Phe Leu Tyr His Val Ala Gly Phe Leu Leu Pro Met Leu Val
                595                     600                 605

ATG GGC TGG TGC TAC GTG GGG GTA GTG CAC AGG TTG CGC CAG GCC CAG         831
Met Gly Trp Cys Tyr Val Gly Val Val His Arg Leu Arg Gln Ala Gln
            610                     615                 620

CGG CGC CCT CAG CGG CAG AAG GCA GTC AGG GTG GCC ATC CTG GTG ACA         879
Arg Arg Pro Gln Arg Gln Lys Ala Val Arg Val Ala Ile Leu Val Thr
625                     630                     635

AGC ATC TTC TTC CTC TGC TGG TCA CCC TAC CAC ATC GTC ATC TTC CTG         927
Ser Ile Phe Phe Leu Cys Trp Ser Pro Tyr His Ile Val Ile Phe Leu
640                     645                     650                 655

GAC ACC CTG GCG AGG CTG AAG GCC GTG GAC AAT ACC TGC AAG CTG AAT         975
Asp Thr Leu Ala Arg Leu Lys Ala Val Asp Asn Thr Cys Lys Leu Asn
                    660                     665                 670

GGC TCT CTC CCC GTG GCC ATC ACC ATG TGT GAG TTC CTG GGC CTG GCC        1023
Gly Ser Leu Pro Val Ala Ile Thr Met Cys Glu Phe Leu Gly Leu Ala
                675                     680                 685

CAC TGC TGC CTC AAC CCC ATG CTC TAC ACT TTC GCC GGC GTG AAG TTC        1071
```

```
His Cys Cys Leu Asn Pro Met Leu Tyr Thr Phe Ala Gly Val Lys Phe
            690                 695                 700

CGC AGT GAC CTG TCG CGG CTC CTG ACC AAG CTG GGC TGT ACC GGC CCT     1119
Arg Ser Asp Leu Ser Arg Leu Leu Thr Lys Leu Gly Cys Thr Gly Pro
705                 710                 715

GCC TCC CTG TGC CAG CTC TTC CCT AGC TGG CGC AGG AGC AGT CTC TCT     1167
Ala Ser Leu Cys Gln Leu Phe Pro Ser Trp Arg Arg Ser Ser Leu Ser
720                 725                 730                 735

GAG TCA GAG AAT GCC ACC TCT CTC ACC ACG TTC TAGGTCCCAG TGTCCCCTTT   1220
Glu Ser Glu Asn Ala Thr Ser Leu Thr Thr Phe
                740                 745

TATTGCTGCT TTTCCTTGGG GCAGGCAGTG ATGCTGGATG CTCCTTCCAA CAGGAGCTGG   1280

GATCCTAAGG GCTCACCGTG GCTAAGAGTG TCCTAGGAGT ATCCTCATTT GGGGTAGCTA   1340

GAGGAACCAA CCCCATTTCT GAACATCCC TGCCAGCTCT TCTGCCGGCC CTGGGGCTAG    1400

GCTGGAGCCC AGGGAGCGGA AAGCAGCTCG AAGGCACAGT GAAGGCTGTC CTTACCCATC   1460

TGCACCCCCC TGGGCTGAGA GAACCTCACG CACCTCCCAT CCTAATCATC AATGCTCAA    1520

GAAACAACTT CTACTTCTGC CCTTGCCAAC GGAGAGCGCC TGCCCCTCCC AGAACACACT   1580

CCATCAGCTT AGGGGCTGCT GACCTCCACA GCTTCCCCTC TCTCCTCCTG CCCACCTGTC   1640

AAACAAAGCC AGAAGCTGAG CACCAGGGGA TGAGTGGAGG TTAAGGCTGA GGAAAGGCCA   1700

GCTGGCAGCA GAGTGTGGCT TCGGACAACT CAGTCCCTAA AAACACAGAC ATTCTGCCAG   1760

GCCCCCAAGC CTGCAGTCAT CTTGACCAAG CAGGAAGCTC AGACTGGTTG AGTTCAGGTA   1820

GCTGCCCCTG GCTCTGACCG AAACAGCGCT GGGTCCACCC CATGTCACCG GATCCTGGGT   1880

GGTCTGCAGG CAGGGCTGAC TCTAGGTGCC CTTGGAGGCC AGCCAGTGAC CTGAGGAAGC   1940

GTGAAGGCCG AGAAGCAAGA AAGAAACCCG ACAGAGGGAA GAAAAGAGCT TTCTTCCCGA   2000

ACCCCAAGGA GGGAGATGGA TCAATCAAAC CCGGCTGTCC CCTCCGCCCA GGCGAGATGG   2060

GGTGGGGGGA GAACTCCTAG GGTGGCTGGG TCCAGGGGAT GGGAGGTTGT GGGCATTGAT   2120

GGGGAAGGAG GCTGGCTTGT CCCCTCCTCA CTCCCTTCCC ATAAGCTATA GACCCGAGGA   2180

AACTCAGAGT CGGAACGGAG AAAGGTGGAC TGGAAGGGGC CCGTGGGAGT CATCTCAACC   2240

ATCCCCTCCG TTGGCATCAC CTTAGGCAGG GAAGTGTAAG AAACACACTG AGGCAGGAAC   2300

TCCCAGGCCC AGGAAGCCGT GCCCTGCCCC CGTGAGGATG TCACTCAGAT GGAACCGCAG   2360

GAAGCTGCTC CGTGCTTGTT TGCTCACCTG GGGTGTGGGA GGCCCGTCCG GCAGTTCTGG   2420

GTGCTCCCTA CCACCTCCCC AGCCTTTGAT CAGGTGGGGA GTCAGGGACC CCTGCCCTTG   2480

TCCCACTCAA GCCAAGCAGC CAAGCTCCTT GGGAGGCCCC ACTGGGGAAA TAACAGCTGT   2540

GGCTCACGTG AGAGTGTCTT CACGGCAGGA CAACGAGAAA GCCCTAAGAC GTCCCTTTTT   2600

TCTCTGAGTA TCTCCTCGCA AGCTGGGTAA TCGATGGGGA GTCTGAAGCA GATGCAAAGA   2660

GGCAGAGGAT GGATTTTGAA TTTTCTTTTT AATAAAAAGG CACCTATAAA ACAGGTCAAT   2720

ACAGTACAGG CAGCACAGAG ACCCCCGGAA CAAGCCTAAA AATTGTTTCA AAATAAAAAC   2780

CAAGAAGATG TCTTCAAAAA AAAAAAAAAA AAAAAAA                          2818
```

(2) INFORMATION FOR SEQ ID NO:8:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asn Tyr Pro Leu Thr Leu Glu Met Asp Leu Glu Asn Leu Glu Asp
 1               5                  10                  15

Leu Phe Trp Glu Leu Asp Arg Leu Asp Asn Tyr Asn Asp Thr Ser Leu
             20                  25                  30

Val Glu Asn His Leu Cys Pro Ala Thr Glu Gly Pro Leu Met Ala Ser
         35                  40                  45

Phe Lys Ala Val Phe Val Pro Val Ala Tyr Ser Leu Ile Phe Leu Leu
     50                  55                  60

Gly Val Ile Gly Asn Val Leu Val Leu Val Ile Leu Glu Arg His Arg
 65                  70                  75                  80

Gln Thr Arg Ser Ser Thr Glu Thr Phe Leu Phe His Leu Ala Val Ala
                 85                  90                  95

Asp Leu Leu Leu Val Phe Ile Leu Pro Phe Ala Val Ala Glu Gly Ser
             100                 105                 110

Val Gly Trp Val Leu Gly Thr Phe Leu Cys Lys Thr Val Ile Ala Leu
         115                 120                 125

His Lys Val Asn Phe Tyr Cys Ser Ser Leu Leu Leu Ala Cys Ile Ala
 130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                 165                 170                 175

Gly Phe Leu Leu Ala Leu Pro Glu Ile Leu Phe Ala Lys Val Ser Gln
             180                 185                 190

Gly His His Asn Asn Ser Leu Pro Arg Cys Thr Phe Ser Gln Glu Asn
         195                 200                 205

Gln Ala Glu Thr His Ala Trp Phe Thr Ser Arg Phe Leu Tyr His Val
     210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                 245                 250                 255

Ala Val Arg Val Ala Ile Leu Val Thr Ser Ile Phe Phe Leu Cys Trp
             260                 265                 270

Ser Pro Tyr His Ile Val Ile Phe Leu Asp Thr Leu Ala Arg Leu Lys
         275                 280                 285

Ala Val Asp Asn Thr Cys Lys Leu Asn Gly Ser Leu Pro Val Ala Ile
     290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                 325                 330                 335

Leu Thr Lys Leu Gly Cys Thr Gly Pro Ala Ser Leu Cys Gln Leu Phe
             340                 345                 350

Pro Ser Trp Arg Arg Ser Ser Leu Ser Glu Ser Glu Asn Ala Thr Ser
         355                 360                 365

Leu Thr Thr Phe
370
```

MODULATING THE INTERACTION OF THE CHEMOKINE, B LYMPHOCYTE HEMOATTRACTANT, AND ITS RECEPTOR, BLR1

This invention was made with Government support under Grant No. AI40098, awarded by the National Institutes of Health. The Government has certain rights in this invention.

FIELD OF THE INVENTION

The field of this invention is methods for modulating immune cell function.

BACKGROUND

Homing of B lymphocytes into specialized microenvironments within secondary lymphoid tissues is essential for normal immune function, yet the molecular cues guiding this cellular traffic are not well defined. Evidence suggests the involvement of chemokines (1–5), but no chemokine has been shown to have the required expression pattern or chemoattractant activity (6). Here we describe a chemokine, B Lymphocyte Chemoattractant (BLC), that is highly expressed in the follicles of Peyer's patches, spleen and lymph nodes. BLC strongly attracts B lymphocytes while promoting migration of only small numbers of T cells and macrophages and therefore is the first chemokine identified with selectivity for B cells. Recently an orphan chemokine receptor, Burkitt's Lymphoma Receptor 1 (BLR1) was found to be required for B cell migration into lymphoid follicles (4). We also disclose that BLC stimulates calcium influx and chemotaxis in cells transfected with BLR1, indicating that BLC functions as a BLR1 ligand and guides B lymphocytes to follicles in secondary lymphoid organs. BLR1:BLC interactions provide a valuable target for pharmaceutical development and therapeutic intervention.

RELEVANT LITERATURE

Förster et al, 1996, Cell 87, 1037–1047, describe the functions of BLR1 as inferred from a knock-out mouse. Guegler et al., 1997, U.S. Pat. No. 5,633,149 describe a gene specific to inflamed adenoid tissue inferred to encode a protein, ADEC, with sequence similarity to a native BLC.

SUMMARY OF THE INVENTION

The invention provides methods and compositions for modulating and identifying agents which modulate the interaction of BLR1 and BLC polypeptides. The methods for identifying BLR1:BLC modulators find particular application in commercial drug screens. These methods generally comprise combining BLR1 and BLC polypeptides with a candidate agent under conditions whereby, but for the presence of the agent, the polypeptides engage in a first interaction, and determining a second interaction of the polypeptides in the presence of the agent, wherein a difference between the first and second interactions indicates that the agent modulates the interaction of the polypeptides. The subject methods of modulating the interaction of BLR1 and BLC polypeptides involve combining BLR1 and BLC polypeptides expressed in other than adenoid tissue with a modulator, under conditions whereby, but for the presence of the modulator, the polypeptides engage in a first interaction, and whereby the polypeptides engage in a second interaction different from the first interaction. In a particular embodiment, the modulator is an antagonistic, esp. dominant negative, form of the BLC polypeptide. The invention also provides compositions useful in the subject methods, such as in vitro mixtures comprising BLR1 and BLC polypeptides.

BRIEF DESCRIPTION OF THE FIGURES

FIG. 1a show migration of B cells; FIG. 1b, CD4+T cells; FIG. 1c, CD8+T cells; FIG. 1d; granulocytes; and FIG. 1e, monocytes/macrophages to BLC. Positive controls are SDF1a (FIGS. 1a, b, c, e) and IL8 (FIG. 1d). FIG. 1f shows the failure of B cells to migrate in the absence of a BLC gradient. BLC was added to the upper or lower chamber of the apparatus as indicated. FIG. 1g, shows inhibition of BLC-induced migration by pretreatment of cells with pertussis toxin (PTX). Data points with error bars represent the mean 1 s.d. for triplicates; individual data points are shown for duplicates. Each experiment was performed a minimum of two times.

FIG. 2(a)–(f). BLR1-mediated calcium mobilization and chemotaxis in response to BLC. HEK 293 cells, stably transfected with the indicated chemokine receptors (FIGS. 2a–d), were loaded with the calcium probe Indo-1 and assayed by spectrofluorimetry for changes in intracellular calcium in response to BLC. FIG. 2a, Calcium flux as a function of BLC concentration (nM). FIG. 2b, Specificity of the response of BLR1 to BLC. FIG. 2c, Lack of response to BLC in CCR1-transfected cells. FIG. 2d, Lack of response to BLC in CXCR2-transfected cells. FIG. 2e, Percentage of maximal calcium flux as a function of BLC concentration in BLR1-transfected 300–19 cells. FIG. 2f, Chemotactic response of BLR1-transfected Jurkat cells to BLC. Results of chemotaxis are expressed as in FIG. 1.

DETAILED DESCRIPTION OF THE INVENTION

Figure 1A:
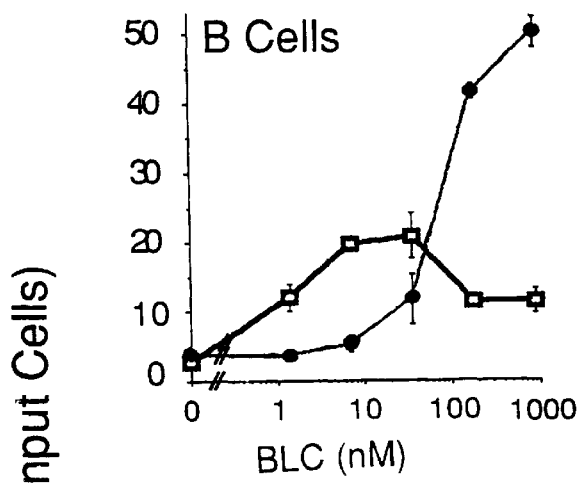
FIGS. 1(a)–(g). Chemotactic activity of BLC on leukocyte subtypes. Results are expressed as the percentage of input cells of each subtype migrating to the lower chamber of a Transwell filter.

The invention provides efficient methods of identifying agents, compounds or lead compounds for agents active at the level of a BLR1:BLC modulatable cellular function, particularly in vitro assays for agents, including agonists and antagonists, which alter the receptor:ligand binding of BLR1 and BLC polypeptides. A wide variety of in vitro assays for binding agents are provided including labeled proteinprotein binding assays, immunoassays, cell based assays, etc. In one aspect, the methods involve forming a mixture of BLR1 and BLC polypeptides and a candidate agent, and determining the effect of the agent on the interactions of the BLR1 and BLC polypeptides. The methods are amenable to automated, cost-effective high throughput screening of chemical libraries for lead compounds. Identified reagents find use in the pharmaceutical industries for animal and human trials; for example, the reagents may be derivatized and rescreened in in vitro and/or in situ (animal) assays to optimize activity and minimize toxicity for pharmaceutical development.

The BLR1 polypeptides of the assays, which may be part of a fusion product with another peptide or polypeptide, e.g. a tag for detection or anchoring, etc., are generally provided as transmembrane proteins, on liposomes, cells, isolated phospholipid membranes, etc. A wide variety of molecular and biochemical methods for biochemical synthesis, molecular expression and purification of the subject compositions, including the expression of heterologous recombinant proteins in cells, including bacterial cells (e.g.

E. coli), yeast (e.g. S. Cerevisiae), animal cells (e.g. CHO, 3T3, BHK, baculovirus-compatible insect cells, etc.) see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) and incorporation of polypeptides into liposomes, are described or referenced herein or are otherwise known in the art. The nucleotide sequences of exemplary natural cDNAs encoding mouse and human BLR1 polypeptides are shown as SEQ ID NOS: 5 and 7, respectively, and the full conceptual translates are shown as SEQ ID NOS:6 and 8. The BLR1 polypeptides may be deletion mutants of SEQ ID NOS:6 or 8 which retain BLC specific binding activity. BLC-specific binding is readily determined by convenient in vitro binding assays, in vitro cell-based assays, or in vivo assays in animals (e.g. transgenics, etc.), etc. In one embodiment, BLR1 polypeptide-encoding constructs comprising SEQ ID NO:5 or 7 are expressed in COS cells and assayed for binding to radiolabeled BLC ligands (Table 1).

TABLE 1

BLC-specific BLR1 polypeptides. BLR1 polypeptide-encoding constructs are expressed in COS cells and assayed for binding to radiolabeled BLC ligand.

| BLR1 Polypeptide, Sequence | BLC Binding |
| --- | --- |
| SEQ ID NO:6, residues 5-371 | +++ |
| SEQ ID NO:6, residues 4-366 | +++ |
| SEQ ID NO:6, residues 3-361 | +++ |
| SEQ ID NO:6, residues 2-356 | +++ |
| SEQ ID NO:6, residues 1-351 | +++ |
| SEQ ID NO:8, residues 5-371 | +++ |
| SEQ ID NO:8, residues 4-366 | +++ |
| SEQ ID NO:8, residues 3-361 | +++ |
| SEQ ID NO:8, residues 2-356 | +++ |
| SEQ ID NO:8, residues 1-351 | +++ |

The BLC polypeptides are generally provided in soluble form. The nucleotide sequences of exemplary natural cDNAs encoding mouse and human BLC polypeptides are shown as SEQ ID NOS: 1 and 3, respectively, and the full conceptual translates are shown as SEQ ID NOS:2 and 4. The BLC polypeptides may be deletion mutants of SEQ ID NOS:2 or 4 which retain BLR1 specific binding activity. Molecular and biochemical methods for biochemical synthesis, molecular expression and purification of the subject compositions are known in the art (supra). BLR1-specific binding is readily determined by convenient in vitro, cell-based, or in vivo assays: e.g. in vitro binding assays, cell culture assays, in animals (e.g. transgenics, etc.), etc. In one embodiment, radiolabled BLC polypeptides are assayed for binding to BLR1 polypeptides expressed on COS cells (Table 2).

TABLE 2

BLR1-specific BLC polypeptides. Radiolabled BLC polypeptides are assayed for binding to BLR1 polypeptides expressed on COS cells.

| BLC Polypeptide Sequence | BLR1 Binding |
| --- | --- |
| SEQ ID NO:2, residues 1-103 | +++ |
| SEQ ID NO:2, residues 1-98 | +++ |
| SEQ ID NO:2, residues 1-93 | +++ |
| SEQ ID NO:2, residues 5-108 | +++ |
| SEQ ID NO:2, residues 10-108 | +++ |
| SEQ ID NO:4, residues 1-104 | +++ |

TABLE 2-continued

BLR1-specific BLC polypeptides. Radiolabled BLC polypeptides are assayed for binding to BLR1 polypeptides expressed on COS cells.

| BLC Polypeptide Sequence | BLR1 Binding |
| --- | --- |
| SEQ ID NO:4, residues 1-99 | +++ |
| SEQ ID NO:4, residues 1-94 | +++ |
| SEQ ID NO:4, residues 5-109 | +++ |
| SEQ ID NO:4, residues 10-109 | +++ |

In other embodiments, BLC polypeptides are screened for chemotactic activity. Methods for measuring chemotactic activity of BLC polypeptides are well known in the art, see e.g. U.S. Pat No. 5,633,149. For example, activity may be measured in 48-well microchemotaxis chambers according to Falk W. R. et al (1980) J Immunol Methods 33:239. In each well, two compartments are separated by a filter that allows the passage of cells in response to a chemical gradient. Cell culture medium such as RPMI 1640 containing the BLC polypeptide is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing the BLC polypeptides are typed and quantified.

The specificity of the chemoattraction may be determined by performing the chemotaxis assay on specific populations of cells. In one example, blood cells obtained from venipuncture are fractionated by density gradient centrifugation and the chemotactic activity of BLC polypeptides is tested on enriched populations of neutrophils, peripheral blood mononuclear cells, monocytes and lymphocytes. Optionally, such enriched cell populations are further fractionated using CD8+ and CD4+ specific antibodies for negative selection of CD4+ and CD8+ enriched T-cell populations, respectively. Another assay elucidates the chemotactic effect of BLC polypeptides on activated T-cells. For example, unfractionated T-cells or fractionated T-cell subsets may be cultured for 6 to 8 hours in tissue culture vessels coated with CD-3 antibody. After this CD-3 activation, the chemotactic activity of the BLC polypeptides are tested as described above. Other methods for obtaining enriched cell populations are known in the art.

Some chemokines also produce a non-chemotactic cell activation of neutrophils and monocytes. This may be tested via standard measures of neutrophil activation such as actin polymerization, increase in respiratory burst activity, alegranulation of the azurophilic granule and mobilization of $Ca^{2+}$ as part of the signal transduction pathway. An assay for mobilization of $Ca^{2+}$ involves preloading neutrophils with a fluorescent probe whose emission characteristics have been altered by $Ca^{2+}$ binding. When the cells are exposed to an activating stimulus, $Ca^{2+}$ flux is determined by observation of the cells in a fluorometer. The measurement of $Ca^{2+}$ mobilization has been described in Gpynkievicz G. et al. (1985) J Biol Chem 260:3440, and McColl S. et al. (1993) J Immunol 150:4550–4555. Degranulation and respiratory burst responses are also measured in monocytes (Zachariae C. O. C. et al. (1990) J Exp Med 171:2177–82). Further measures of monocyte activation are regulation of adhesion molecule expression and cytokine production (Jiang Y. et al. (1992) J Immunol 148: 2423–8). Expression of adhesion molecules also varies with lymphocyte activation (Taub. D. et al. (1993) Science 260: 355–358).

In certain embodiments, the BLC and BLR1 polypeptides are encoded by nucleic acids comprising SEQ ID NO:1 or 3, and SEQ ID NO:5 or 7, respectively, or nucleic acids which hybridize with full-length strands thereof, preferably under stringent conditions. The invention also provides nucleic acid hybridization probes and replication/amplification primers having a BLC cDNA specific sequence comprising SEQ ID NO:1, 3, 5 or 7 and sufficient to effect specific hybridization thereto (i.e. specifically hybridize with SEQ ID NO:1, 3, 5 or 7, respectively). These probes/primers find diagnostic uses for detecting BLC expression in nonadenoid tissue. Such nucleic acids are at least 36, preferably at least 72, more preferably at least 144 and most preferably at least 288 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE (Conditions I); preferably hybridizing in a buffer comprising 50% formamide in 5×SSPE buffer at a temperature of 42° C. and remaining bound when subject to washing at 42° C. with 0.2×SSPE buffer at 42° C. (Conditions II).

The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the BLR1 and BLC polypeptides interact or bind with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the BLR1 and BLC polypeptides is detected by any convenient way. Where at least one of the polypeptides comprises a label, the label may provide for direct detection as radioactivity, luminescence, fluorescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the polypeptides in the absence of the agent as compared with the binding affinity in the presence of the agent indicates that the agent modulates the binding of the BLR1 and BLC polypeptides. A difference, as used herein, is statistically significant and preferably represents at least a 10%, more preferably at least a 50%, most preferably at least a 90% difference.

The invention also provides methods for modulating the interaction of BLR1 and BLC polypeptides. In a particular embodiment, the BLR1 is expressed on the surface of a cell, which may reside in culture or in situ, i.e. within the natural host. The methods involve combining the BLR1 and BLC polypeptides with a modulator which alters their interaction. In preferred in situ applications, the BLR1 and BLC polypeptides are endogenous (naturally expressed by cells at the target site), the modulator is exogenous (not naturally present at the target site) and the target site is other than adenoid tissue. Exemplary modulators include BLC-specific antibodies, antagonistic or dominant negative BLC deletion mutants, antisense nucleic acids and ribozymes derived from SEQ ID NOS:1 and 3, agents identified in the foregoing screens, etc. The invention provides a wide variety of approaches to modulate, especially inhibit, BLC function in situ.

As disclosed herein, the chemotactic function of BLC depends on BLC gradients within lymphoid and other tissues, and treatment with BLC polypeptides is shown to disrupt in vivo BLC gradients. The invention provides a wide variety of BLC polypeptides. For example, in one embodiment, the invention provides BLC polypeptides with enhanced in vivo half-life isolated from mutagenesis screens for decreased binding to the Duffy antigen, a chemokine clearance receptor expressed on red blood cells, and attachment to immunoglobulin (Ig).

In another embodiment, the invention provides N-terminal truncated BLC deletion mutants having antagonistic function. Deletion of 8 residues from the amino terminus of the CC chemokine RANTES established a molecule with potent antagonistic activity (J. Biol. Chem. 271, 10521). Antagonistic properties of some viral chemokines have also been related to truncations of the amino terminus (Proc. Natl. Acad. Sci. 94, 9875). Similarly, N-terminal deletion mutants of BLC lacking from 1–10 amino terminal amino acids demonstrate antagonistic activity in chemotaxis assays performed with lymphocytes from mouse spleen and baculovirus-expressed BLC, Table 3.

TABLE 3

N-terminal deletion mutant BLC antagonists.

| Deletion Mutant | Antagonist Activity |
| --- | --- |
| Δ1 BLC (N-terminus 3 residue truncation) | + |
| Δ2 BLC (N-terminus 4 residue truncation) | ++ |
| Δ3 BLC (N-terminus 5 residue truncation) | +++ |
| Δ4 BLC (N-terminus 6 residue truncation) | +++ |
| Δ5 BLC (N-terminus 7 residue truncation) | +++ |
| Δ6 BLC (N-terminus 8 residue truncation) | +++ |
| Δ7 BLC (N-terminus 9 residue truncation) | +++ |
| Δ8 BLC (N-terminus 10 residue truncation) | +++ |
| Δ9 BLC (C-terminus 3 residue truncation) | − |
| Δ10 BLC (C-terminus 5 residue truncation) | − |

In another embodiment, antagonistic BLC polypeptides are generated by substitution screens of selected BLC residues. Antagonists of IL8 and CINC have been made by replacing the ELR sequence preceding the CXC motif with the sequence AAR and simultaneously truncating the amino terminal 5 amino acids (J. Biol. Chem. 268, 7125; J. Immunol. 159, 1059). Similarly, a BLC antagonist will be created by replacing the NLK sequence preceding the CXC motif with AAR or AAK and truncating the 5 amino terminal amino acids. In addition, appending additional residues, especially N-terminal residues can generate antagonists, as shown with recombinant human RANTES retaining the initiating methionine (Proudfoot A E, et al, J Biol Chem Feb. 2, 1996; 271(5):2599–2603). Substitutions made based on comparison of BLC with viral chemokine antagonists (Science 277, 1656; Proc. Natl. Acad. Sci. 94, 9875) also produce BLC antagonists. Accordingly, differences in amino acid sequence between viral antagonists and conserved residues in the CXC chemokine family, especially amino acids that lead to charge inversions, hydrophobicity changes or structural changes are introduced into BLC to generate antagonists.

BLC antagonists are also generated by chemical modifications. A derivative of RANTES created by chemical modification of the amino terminus, aminooxypentane (AOP)-RANTES, is a potent RANTES antagonist (Simmons G, et al., 1997, Science 276, 276–279). Similarly, modification of BLC by attachment of this or other small organic molecules generates structures with antagonistic activity.

Modified BLC polypeptides may also be used to retain BLC receptors within cells and so reduce the responsiveness of the cell to BLC. For example, BLC may be expressed as a fusion with a terminal KDEL or related endoplasmic reticulum (ER) retention signal, with or without a linker sequence. Such modification of the CXC chemokine SDF1a leads to intracellular retention of receptor CXCR4 and reduced cell responsiveness to the chemokine (Nat. Med. 3, 1110). A related strategy involves attachment of BLC to a transmembrane and cytoplasmic sequence from an ER retained transmembrane protein, such as the adenovirus E19 protein.

For in situ applications, the subject compositions, including agents and modulators (e.g. BLC antagonists), may be administered in any convenient way, wherein the dosage, route and site of administration are determined by the targeted disease. For example, antagonist proteins generated by mutation or chemical modification may be inoculated intravenously or subcutaneously, by inhalation or ingestion, or applied topically. Intravenous administration is a preferred route of treatment for systemic diseases such as AIDS and lymphomas/leukemias. Local administration is preferred when only one or a small number of sites are affected, such as treatment of certain joints in rheumatoid arthritis patients. Gene therapy approaches are used for the introduction of intracellulary retained chemokines, e.g. peripheral blood T cells or hematopoietic stem cells removed from AIDS patients are transfected or retrovirally infected with the BLC construct and then refused.

In one embodiment, the subject polypeptides are amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic polypeptides. Generally, the amount administered will be empirically determined, typically in the range of about 10 to 1000 $\mu$g/kg of the recipient and the concentration will generally be in the range of about 50 to 500 $\mu$g/ml in the dose administered. Other additives may be included, such as stabilizers, bactericides, etc. will be present in conventional amounts.

The compositions are frequently administered in combination with a pharmaceutically acceptable excipient, carrier, diluent, etc., such as sterile saline or other medium, gelatin, an oil, etc. to form pharmaceutically acceptable compositions, and such administration may be provided in single or multiple dosages. Useful carriers include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations for polypeptide-based therapeutics is known in the art. The compositions may be provided in any convenient form and/or pharmaceutically acceptable dosage units/unit containers, including tablets, pills, capsules, troches, powders, sprays, creams, etc. The compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics*, 9th Ed., 1996, McGraw-Hill.

Exemplary indications and therapeutic strategies are described below:

Infection: Natural BLC functions to attract cells into lymphoid follicles, sites where large amounts of HIV are trapped in infected patients. Blocking the response of T cells to BLC reduces or inhibits entry of T cells into follicles and so reduces or inhibits access to these viral reservoirs. Accordingly, treatment of individuals infected with HIV (or other T tropic viruses) includes the systemic inoculation of BLC and BLC antagonists or introduction of ER-retained BLC by gene therapy. Such treatment may be performed in combination with other anti-HIV therapies. In another example, anti-BLC agents offer novel therapeutic approaches to viruses that have exploited the strong chemoattractant property of BLC-like chemokines to attract target cells for infection, e.g. Marek's Disease Virus, which is transmitted by inhalation but rapidly infects B cells recruited into the lung.

Lymphoma: Many lymphomas occupy specific niches within lymphoid tissues for long periods before apparently becoming independent of these zones and spreading to other sites. Progression of lymphomas that position in B cell zones of secondary lymphoid tissues, such as mantle cell lymphoma, follicular center lymphoma and Burkitt's lymphoma may be blocked if cell localization is disrupted by BLC or BLC antagonists, administered i.v. or s.c. Such treatment may be performed in combination with other anti-tumor therapies such as chemotherapy or radiotherapy. Treatment with BLC or BLC antagonists also disrupts recirculation and survival of some leukemias, especially B lineage leukemias.

Autoimmune Disease: In several autoimmune diseases, including rheumatoid arthritis, thyroiditis and diabetes, lymphoid follicles form in the inflamed tissue and contribute to the autoimmune pathology. Treatment with BLC or BLC antagonists, either locally or systemically, inhibits formation or persistence of these structures in some cases and thereby reduces the severity of disease. In another example, persistent production of autoantibodies in patients with autoimmune diseases such as Systemic Lupus Erythrematosis and Myasthenia Gravis depends on appropriate positioning of B lymphocytes within lymphoid or other tissues. The BLC-BLR1 interaction is essential for mounting normal antibody responses (in mice) and is also needed for autoantibody production. Treatment with BLC or BLC antagonists inhibits or reduces production of autoantibodies. In yet another example, local accumulation of B lymphocytes in the lungs of patients with lung diseases such as asthma often contributes to the disease process. Treatment with BLC antagonists by any of the above routes, especially by inhalation, reduces B cell recruitment and local antibody production and thereby ameliorates the disease.

The following experimental section and examples are offered by way of illustration and not by way of limitation:

EXAMPLES

BLC Identification and Functional Characterization as BLR1 Ligand

To identify novel chemokines that might play a role in lymphocyte homing we hybridized mouse tissues in situ with anti-sense transcripts of expressed sequence tags (ESTs) having homology to chemokines. One such EST (I.M.A.G.E. Consortium Clone 596050) hybridized strongly to spleen, Peyer's patches and lymph nodes but weakly or not at all to multiple non-lymphoid tissues. We refer to this transcript and the protein it encodes as BLC. In the spleen BLC hybridized to the B cell rich zones, or follicles, present in the outer region of the white pulp cords. A strong signal was detected in a reticular pattern within the follicle and at the outer boundary where the follicle meets the surrounding marginal zone. In Peyer's patches expression of BLC was strongest within germinal centers, sites where B cells undergo somatic mutation and affinity maturation (7), and extended into the surrounding mantle zone. Expression in lymph nodes was again concentrated in a reticular pattern within the follicles although the hybridization signal was variable and was not seen in all follicles. Northern blotting revealed a 1.2 kb transcript in wildtype spleen, Peyer's patches and lymph nodes but not in resting B or T cells. BLC expression was reduced 85% in spleens of lymphocyte-deficient RAG1-knockout mice, suggesting that lymphocytes provide a stimulus that promotes BLC expression in non-lymphoid splenic cells. Accumulation of follicular dendritic cells (FDC) in lymphoid tissues is known to depend on the presence of B and T lymphocytes (8). Furthermore, FDC have extensive processes that extend throughout lymphoid follicles in a pattern similar to the BLC in situ hybridization pattern (9). These findings indicate that FDC may be a source of this novel chemokine.

To identify the full length cDNA for BLC, we searched for ESTs contiguous to the clone used for hybridization. Sequence analysis of four overlapping clones revealed a 1112 bp cDNA (SEQ ID NO:1) containing an open reading that encoded a putative protein of 109 amino acids (SEQ ID NO:2) with a predicted 21 amino acid leader peptide. This sequence contained four cysteines in a pattern typical of the CXC family of chemokines (10) and BLC was found to have strongest similarity to GROa. We also identified a cluster of six human EST clones encoding a protein with 64% amino acid similarity to murine BLC that is human BLC (SEQ ID NOS:3 and 4). A sequence tagged site (STS) derived from this sequence (Genbank #G14456) had been mapped to chromosome segment 4q21 (11), placing the BLC gene in proximity to most known CXC chemokines including IL-8, GRO, IP-10, and PF4 (12). Interestingly, the protein with the greatest similarity to mouse and human BLC is Meq-sp, a product of the Marek's Disease Virus (MDV) Eco Q gene. MDV is a lymphotropic avian herpesvirus that causes a disease common to almost all commercial chicken stocks characterized by the development of lymphomas in multiple organs (13). Meq-sp was identified in MDV infected cells and was not previously recognized to contain a consensus chemokine motif (14).

Figure 1B:
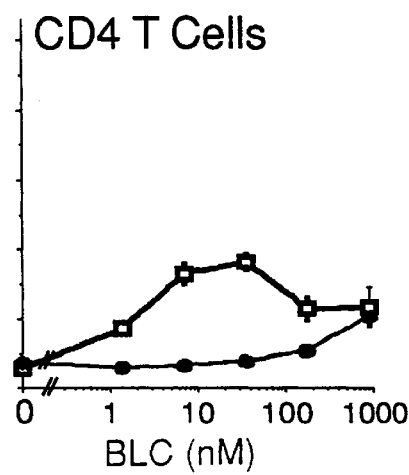
Figure 1C:
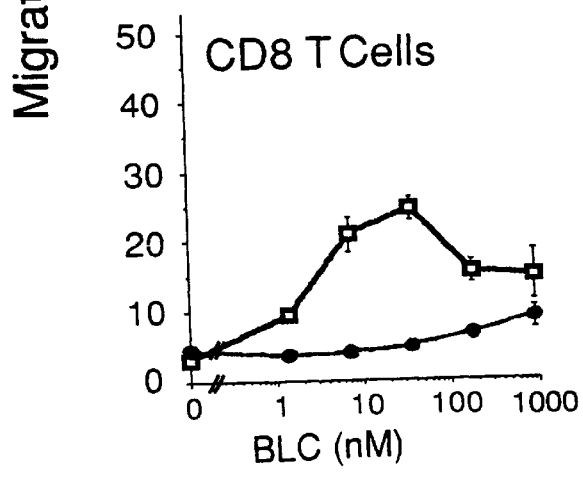
Figure 1D:
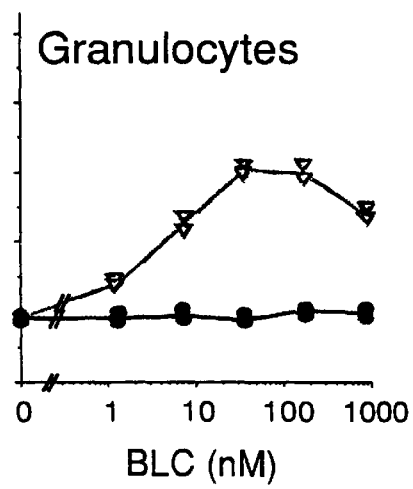
Figure 1E:
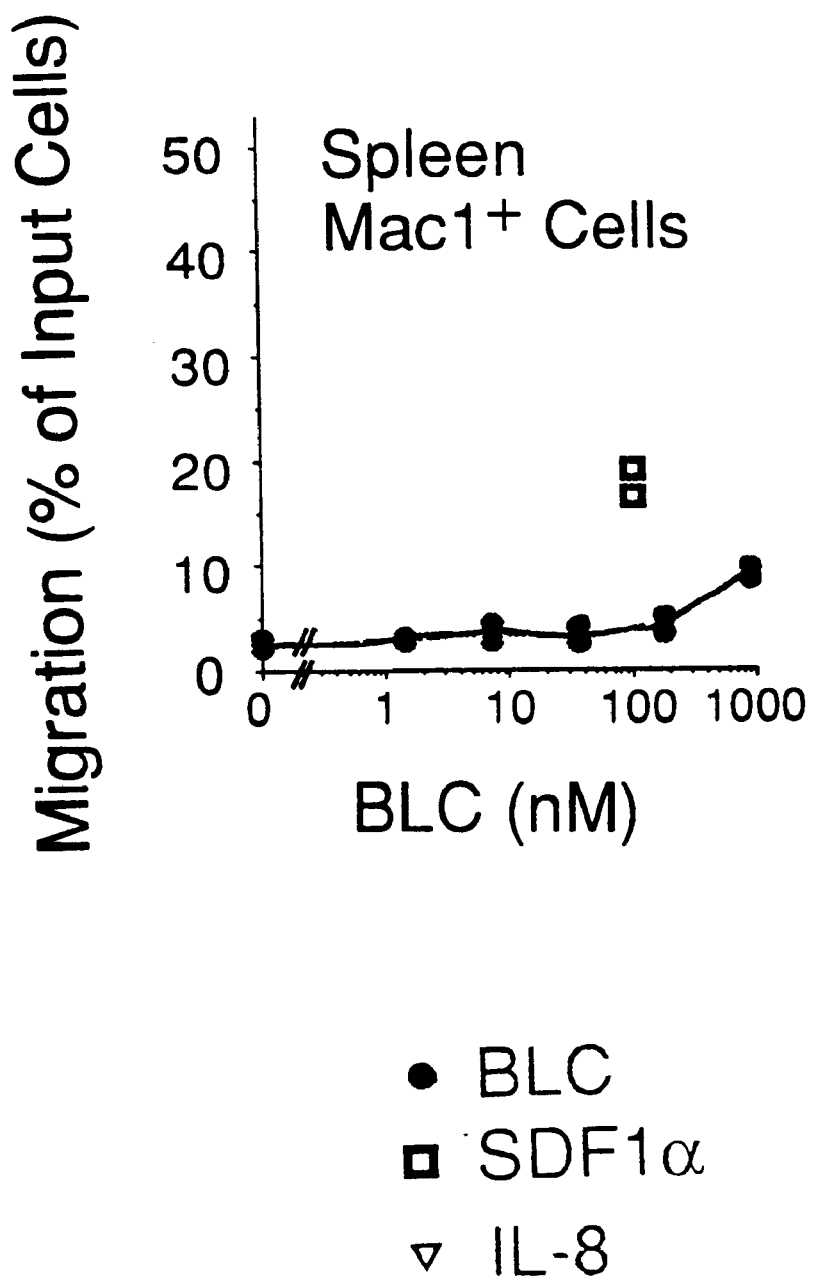

The above findings suggested that BLC may be a B lymphocyte chemoattractant. To test this possibility, chemotaxis assays were performed with lymphocytes from mouse spleen and baculovirus-expressed BLC estimated to be greater than 95% pure by silver staining. BLC induced a strong chemotactic response in B cells (FIG. 1a) while showing limited activity towards CD4 and CD8 T cells (FIG. 1b, c). The response was chemotactic rather than chemokinetic since cells incubated with BLC in the absence of a gradient failed to migrate (FIG. 1f). SDF1a, previously described as the most efficacious chemokine for resting lymphocytes (15), attracted fewer B cells than BLC and lacked any B cell specificity (FIG. 1a–c), highlighting the unique properties of the novel chemokine and leading us to name it BLC for B-Lymphocyte Chemoattractant. BLC had weak but reproducible chemotactic activity for spleen monocytes/macrophages (FIG. 1e) but in contrast to many CXC chemokines, showed no chemotactic activity towards granulocytes (FIG. 1d). Despite its efficacy as a B cell attractant, BLC had a potency less than that of most chemokines, possibly because the baculovirus expressed protein is not fully active. An alternative possibility is that high potency is not required for a chemokine that is expressed constitutively within lymphoid tissues.

Figure 1G:
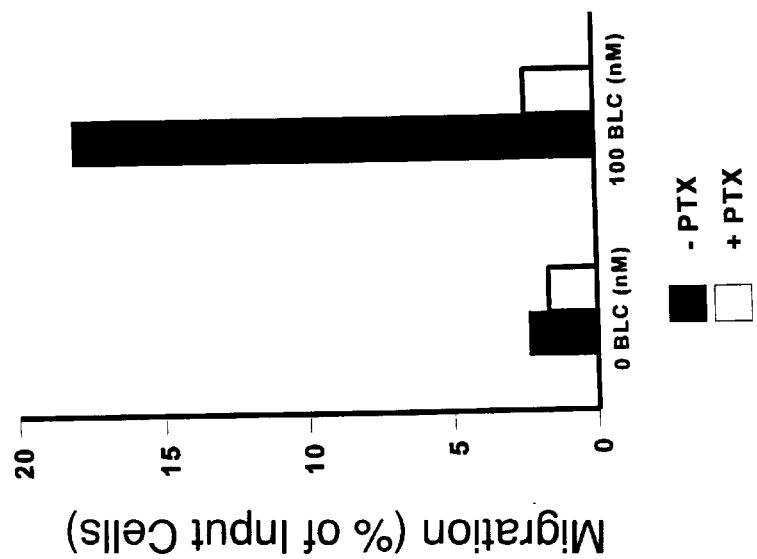
Figure 1F:
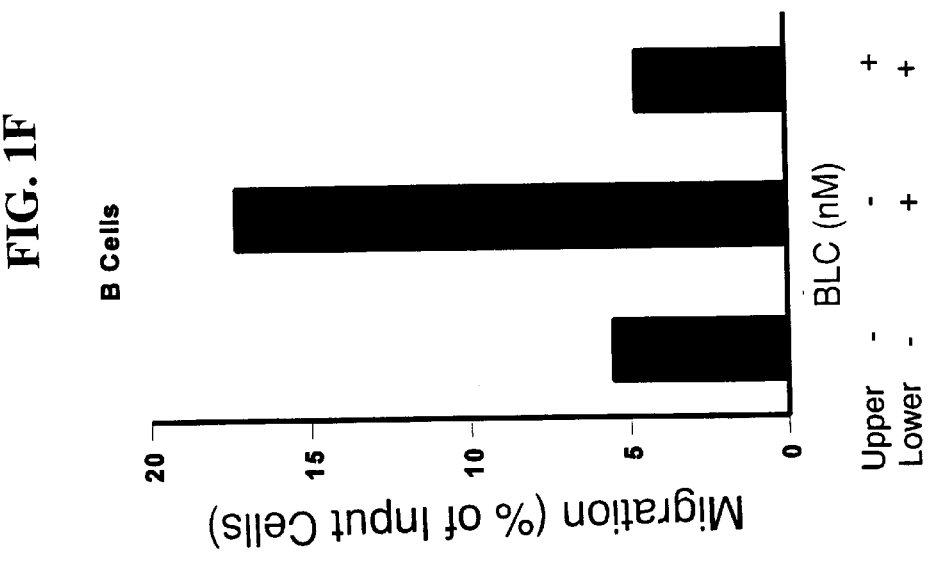
Figure 2A:
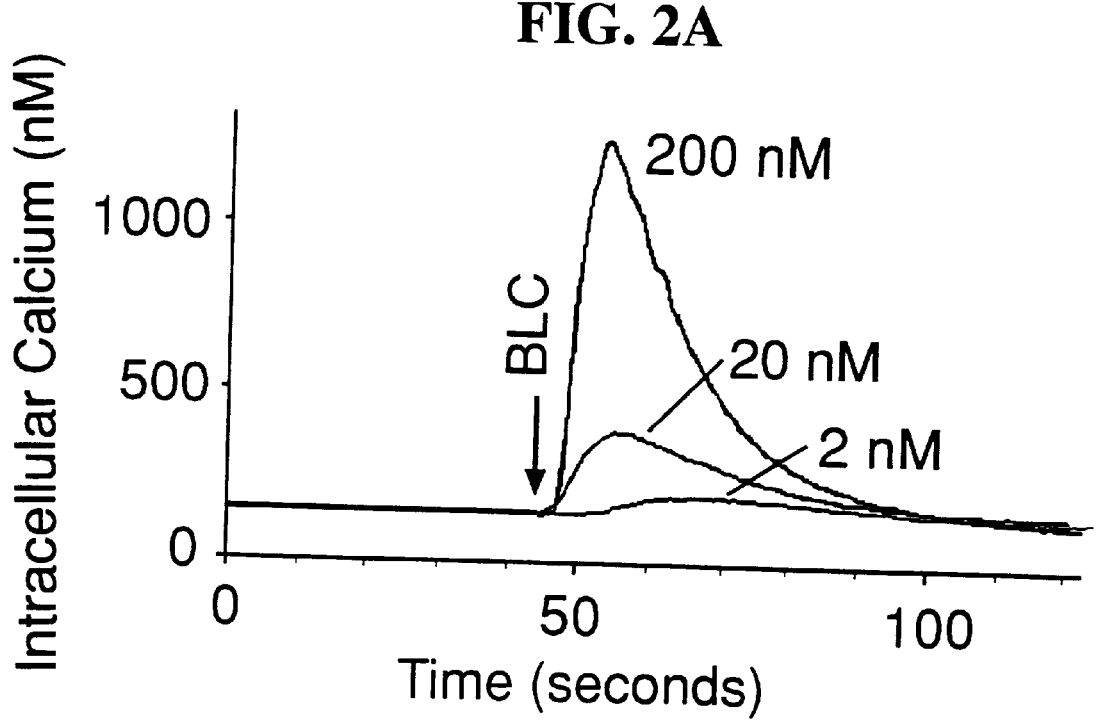
Figure 2B:
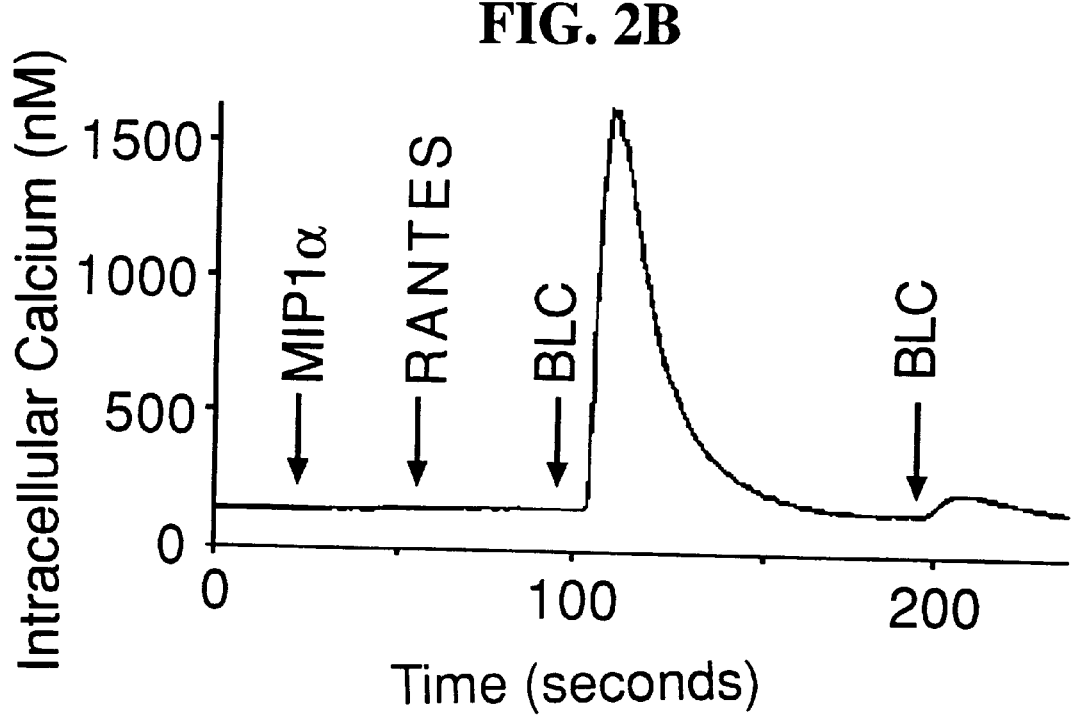
Figure 2C:
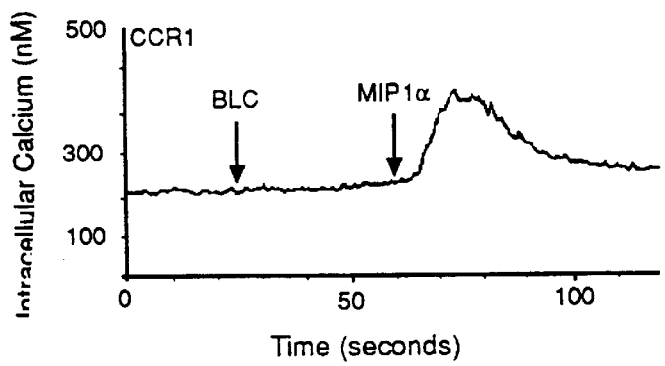
Figure 2D:
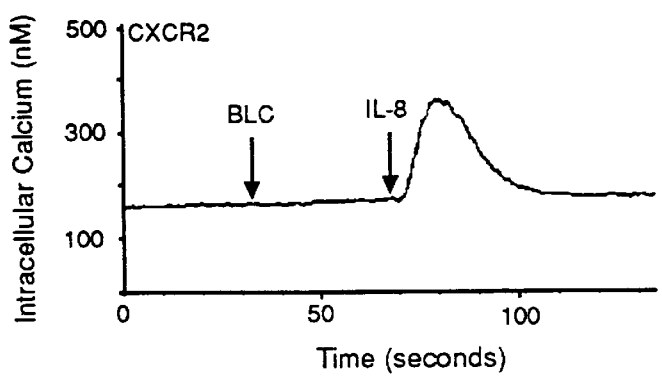
Figure 2E:
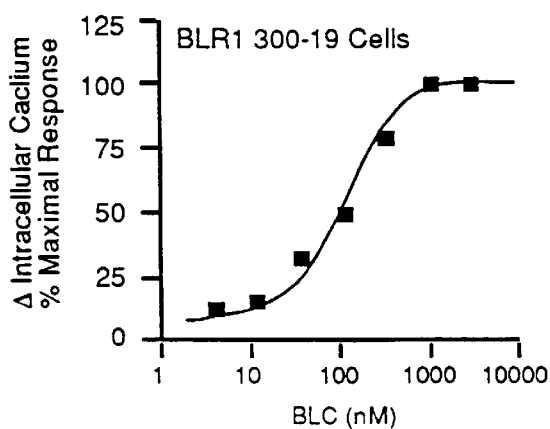

All chemokines studied thus far signal via pertussis toxin sensitive G-protein-coupled receptors (12) and this was also found to be the case for BLC as pertussis toxin pretreated B cells failed to migrate (FIG. 1g). Recent experiments in mice with targeted disruption of the orphan chemokine receptor BLR1, have indicated that this receptor is required for B cell homing to follicles in spleen and Peyer's patches (4). We therefore tested whether BLC could signal through BLR1. Human embryonic kidney 293 cells stably transfected with mouse BLR1 showed a dose dependent calcium flux in response to BLC (FIG. 2a) whereas several other chemokines did not stimulate a response and did not desensitize these cells to BLC (FIG. 2b). BLC failed to stimulate a calcium flux in 293 cells transfected with CCR1, CCR2 or CXCR2 demonstrating that the response of BLR1 transfected cells was specific (FIG. 2c, d). Using BLR1 transfected 300–19 pre-B cells a more complete dose response curve was obtained showing that the response to BLC is saturable (FIG. 2e). Control transfectants of either cell line did not respond to BLC. We next tested the ability of BLC to stimulate chemotaxis through BLR1. Jurkat T cells transfected with BLR1 showed a chemotactic response toward BLC whereas BLR1- negative cells failed to respond (FIG. 2e). Our findings demonstrate that BLR1 confers cells with responsiveness to BLC and that BLC-responsiveness of cells from mouse lymphoid tissues correlates with the reported expression of BLR1 in all B cells and in subsets of T cells and monocytes (4, 16, 17).

In summary, we disclose a novel CXC chemokine, BLC, expressed in the follicles of spleen, Peyer's patches and lymph nodes that is a strong B cell chemoattractant. BLC's expression pattern, chemotactic activity, and ability to stimulate cells expressing BLR1 indicate that it is a physiological BLR1 ligand, acting to direct the migration of B lymphocytes to follicles in secondary lymphoid organs. Although BLR1 is required for B cell migration into splenic and Peyer's patch follicles, it is not needed for B cell localization in lymph node follicles. Taking the results presented here together with the recent identification of chemokines expressed in lymphoid T cell areas that strongly attract resting T cells (18, 19), indicates that chemokines are the major cues promoting cell compartmentalization within lymphoid tissues.

Sequence Analysis. Pattern searches of the NCBI EST database using TFASTA (20) with human MCP-1 as a template retrieved human and mouse EST's for BLC. BLAST (21) searches with these sequences identified contiguous ESTs. I.M.A.G.E. Consortium [LLNL] cDNA clones 596050, 598232, 617961, and 749241 (22) were obtained from Genome Systems Inc (St. Louis, Mo.) as EcoRI-NotI inserts in the pT7T3-Pac vector and sequenced. Similarity scores were calculated using the Blossum 30 matrix.

RNA Expression studies. For Northern analysis, mRNA from mouse tissues or purified cells was subjected to gel electrophoresis, transferred to Hybond-N+ membranes (Amersham), and probed using randomly primed mouse BLC EST 596050, which spans bases 10–532 of the BLC cDNA. For in situ hybridizations, paraffin sections (5 mm) from C57BL/6 mice were deparaffinized, fixed in 4% paraformaldehyde, and treated with proteinase K. After washing in 0.5×SSC, the sections were covered with hybridization solution, prehybridized for 1 to 3 hrs. at 55° C., and hybridized overnight with sense or antisense S35-labeled riboprobe transcribed from the mouse BLC EST 596050. After hybridization, sections were washed at high stringency, dehydrated, dipped in photographic emulsion NTB2 (Kodak), stored at 4° C. for 2–8 weeks, developed, and counterstained with hematoxylin and eosin. In some experiments, frozen sections were hybridized with sense or antisense digoxygenin-labeled riboprobes, immunostained with alkaline phosphatase coupled anti-digoxygenin antibody and developed with NBT/BCIP as described (http://www.cco.caltech.edu/mercer/htmls/Big_In_Situ.html). Immuno-histochemistry with anti-B220 antibody was as described (1).

Production of Recombinant Proteins. The mouse BLC EST 596050 was cloned into the pVL1393 baculovirus transfer vector and co-transfected with BaculoGold (Pharmingen) into SF9 cells according to the manufacturer's instructions. For protein production, SF21 cells were infected at an MOI of 10–20 and cultured in serum-free media for 60 hrs. Conditioned media was cleared, loaded onto a HiTrap heparin affinity column (Pharmacia), and eluted with a 0.2–1M NaCl gradient in 50 mM HEPES (pH 7.9). Fractions containing BLC were pooled, run on a C-1 8 reverse phase HPLC column (Vydac), and eluted with an acetonitrile gradient. SDS PAGE and silver staining of this preparation revealed a single protein band of the expected molecular weight for BLC (10 kD) that represented more than 95% of the total protein. Protein concentration was measured using the Bio-Rad protein assay. Protein sequence analysis identified the isoleucine at position 22 as the amino terminus of the mature recombinant protein.

Chemotaxis. Lymphocytes and macrophages were obtained from spleens of C57BL/6 mice. For macrophage chemotaxis, B cells were depleted by passage over a MACS column (Milteny Biotec, Auburn, Calif.) after incubation with biotinylated anti-B220 antibodies and streptavidin-coated magnetic beads. Granulocytes were obtained from mouse bone marrow suspensions. Mouse BLR1 transfected Jurkat cells were obtained by transfection with pREP4 containing the mouse BLR1 coding region (16), isolated by RT-PCR from mouse spleen RNA, and an amino terminal prolactin leader sequence and FLAG epitope (23). Positive clones were identified using the anti-FLAG antibody M1 (Kodak). Chemotaxis assays were performed as previously described (15) and subsets of migrating cells were identified by flow cytometry using antibodies specific for B220, CD4, CD8 (Pharmingen, San Diego, Calif.) and Mac-1 (Caltag, South San Francisco, Calif.). Granulocytes were identified by their characteristic large side scatter profile. In some experiments, cells were preincubated with 100 ng/ml pertussis toxin (List Biol. Labs, Campbell, Calif.) for 2 hrs at 37° C. IL-8 (R&D Systems, Minneapolis, Minn.) and synthetic human SDF1 a (N33A) synthesized by native chemical ligation (Gryphon Sciences, South San Francisco) were used as positive controls. SDF1a (N33A) has identical activity to native human and mouse SDF1a (24, 25).

Calcium fluorimetry on transfected 293 and 300–19 cells. Native mouse BLR1 was subcloned into pBK-CMV (Stratagene) and used to transfect HEK 293 cells and 300–19 pre-B cells. G418-resistant clones were tested for BLR1 expression using an affinity purified rabbit anti-mouse antiserum that is specific for the BLR1 amino terminus. HEK293 cells expressing CCR1, CCR2 and CXCR2 were from the Cardiovascular Research Institute, UCSF. Ca2+-mobilization studies were performed as described (26) using a Hitachi 4500 spectrometer. Intracellular calcium concentrations were calculated using the Hitachi 4500 Intracellular Cation Measurement program.

1. Cyster, J. G. & Goodnow, C. C., J Exp Med 182, 581–586 (1995).
2. Lyons, A. B. & Parish, C. R., Eur. J. Immunol. 25, 3165–3172 (1995).
3. Goodnow, C. C., et al., Adv Immunol 59, 279–368 (1995).
4. Forster, R., et al., Cell 87, 1–20 (1996).
5. Butcher, E. C. & Picker, L. J., Science 272, 60–66 (1996).
6. Goodnow, C. C. & Cyster, J. G., Curr Biol 7, R219–222 (1997).
7. MacLennan, I. C. M., Annu. Rev. Immunol. 12, 117–139 (1994).
8. Yoshida, K., et al., Eur. J. Immunol. 24, 464–468 (1994).
9. Imai, Y. & Yamakawa, M., Pathology International 46, 807–833 (1996).
10. Bacon, K. B. & Schall, T. J., Int Arch Allergy Immunol 109, 97–109 (1996).
11. Schuler, G., et al., Science 274, 540–546 (1996).
12. Baggiolini, M., et al., Annu. Rev. Immunol. 15, 675–705 (1997).
13. Calnek, B. W., CRC Crit. Rev. Microbiol. 12, 293–320 (1986).
14. Peng, Q., et al., Virology 213, 590–599 (1995).
15. Bleul, C. C., et al., J Exp Med 184, 1101–1109 (1996).
16. Kaiser, E., et al., Eur. J. Immunol. 23, 2532–2539 (1993).
17. Barella, L., et al., Biochem. J. 309, 773–779 (1995).
18. Adema, G. J., et al., Nature 387, 713–717 (1997).
19. Nagira, M., et al., J. Biol. Chem. 272, 19518–19524 (1997).
20. Pearson, W. & Lipman, D. Proc Natl Acad Sci U S A 85, 2444–2448 (1988).
21. Altschul, S., et al., J. Mol. Biol. 215, 403–410 (1990).
22. Lennon, G., et al., Genomics 33, 151–152 (1996).
23. Ishii, K., et al., J. Biol Chem. 268, 9780–9786 (1993).
24. Bleul, C. C., et al., Nature 382, 829–833 (1996).
25. Ueda, H., et al., J. Biol. Chem. 272, 24971 (1997).
26. Myers, S. J., Wong, L. M. & Charo, I. F., J Biol Chem 270, 5786–5792 (1995).

Protocol for Ligand Screening of Transfected COS Cells

1. Prepare the Ligand

Expression Construct: cDNAs encoding targeted BLC polypeptides are tagged with alkaline phosphatase (AP) and subcloned into a 293 expression vector (pCEP4: In Vitrogen).

Transfection: 293 EBNA cells are transfected (CaPO$_4$ method) with the BLC expression constructs. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

Transfection: 293 EBNA cells are transfected (CaPO$_4$ method) with the receptor expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Transfect COS Cells

Seed COS cells (250,000) on 35 mm dishes in 2 ml DME/10% FCS.

18–24 h later, dilute 1 ug of BLR1-encoding DNA (cDNA cloned into pMT21 expression vector) into 200 ul serum-free media and add 6 ul of Lipofectamine (Gibco). Incubate this solution at room temperature for 15–45 min.

Wash the cells 2× with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

III. Ligand Binding Assay

Wash plates of transfected COS cells 1× with cold PBS (plus Ca/Mg)/1% goat serum. Add 1 ml conditioned media neat and incubate 90 min at room temp.

Wash 5× with PBS. Wash 1× alkaline phosphatase buffer (100 mM Tris-Cl, pH 9.5, 100 mM NaCl, 5 mM $MgCl_2$). Prepare alkaline phosphatase reagents: 4.5 ul/ml NBT and 3.5 uI/ml BCIP (Gibco) in alkaline phosphatase buffer.

Incubate 10–30 min, quench with 20 mM EDTA in PBS. Cells that have bound BLC polypeptides are visible by the presence of a dark purple reaction product.

In parallel incubations, positive controls are provided by titrating BLC binding with serial dilutions of the mutant receptor conditioned medium.

IV. Results: Binding of BLC to BLR1

Cell expressing mammalian BLC polypeptides were shown to bind BLR1. No reactivity was observed with control COS cells or with receptor-expressing COS cells in the presence of the conjugated AP but in the absence of the BLC-AP fusion.

Protocol for High Throughput BLR1-BLC Binding Assay

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P BLC polypeptide 10× stock: $10^{-8}$–$10^{-6}$ M "cold" BLC polypeptide supplemented with 200,000–250,000 cpm of labeled BLC (Beckman counter). Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

BLR1: $10^{-7}$–$10^{-5}$ M biotinylated BLR1 expressed on COS cells suspended in PBS.

B. Preparation of assay plates:

Coat with 120 $\mu$l of stock N-Avidin per well overnight at 4° C.

Wash 2 times with 200 $\mu$l PBS.

Block with 150 $\mu$l of blocking buffer.

Wash 2 times with 200 $\mu$l PBS.

C. Assay:

Add 40 $\mu$l assay buffer/well.

Add 10 $\mu$l compound or extract.

Add 10 $\mu$l $^{33}$P-BLC (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 $\mu$M biotinylated BLR1 (0.1–10 pmoles/40 ul in assay buffer)

Incubate 1 hour at room temperature.

Stop the reaction by washing 4 times with 200 $\mu$M PBS.

Add 150 $\mu$M scintillation cocktail.

Count in Topcount.

D. Controls for all assays (located on each plate):

a. Non-specific binding b. Soluble (non-biotinylated BLR1) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying agents that modulate the interaction of a B Lymphocyte Chemoattractant (BLC) polypeptide and a Burkitt's Lymphoma Receptor-1 (BLR1) polypeptide, comprising:

providing a cell expressing a BLR1 polypeptide, wherein the BLR1 polypeptide has the amino acid sequence of a protein encoded by DNA that specifically hybridizes under stringent conditions to a probe complementary to the full length of SEQ ID NO: 5 or 7;

contacting the cell with a BLC polypeptide and a candidate modulatory agent, wherein the BLC polypeptide has the amino acid sequence of a protein encoded by DNA that specifically hybridizes under stringent conditions to a probe complementary to the full length of SEQ ID NO: 1 or 3;

detecting an activity selected from the group consisting of binding of the BLC polypeptide to the BLR1 polypeptide, $Ca^{2+}$ mobilization, and chemotaxis; wherein an identical BLC polypeptide effects said activity at a detectable reference level when contacted with an identical cell under the same conditions in the absence of the candidate agent; and comparing the activity detected in the presence of the candidate agent to said reference level, wherein an increase or decrease in said activity relative to said reference level indicates that the agent modulates the interaction of the BLC and BLR1 polypeptides;

wherein a chemokine having the same amino acid sequence as the BLC polypeptide is capable of
 (a) inducing $Ca^{2+}$ mobilization in HEK-293 cells expressing a reference chemokine receptor, or
 (b) inducing a chemotactic response in Jurkat cells expressing a reference chemokine receptor, the reference chemokine receptor having the amino acid sequence set forth in SEQ ID NO: 6 or 8;

and wherein a reference BLC chemokine having the amino acid sequence set forth in SEQ ID NO: 2 or 4 is capable of
 (a) inducing $Ca^{2+}$ mobilization in HEK-293 cells expressing a chemokine receptor, or
 (b) inducing a chemotactic response in Jurkat cells expressing a chemokine receptor, the chemokine receptor having the same amino acid sequence as the BLR1 polypeptide.

2. A method according to claim 1, wherein the BLC polypeptide has the amino acid sequence of SEQ ID NO: 2, SEQ ID NO: 4, or a fragment of SEQ ID NO: 2 or 4.

3. A method according to claim 1, wherein the BLR1 polypeptide has the amino acid sequence of SEQ ID NO: 6, SEQ ID NO: 8, or a fragment of SEQ ID NO: 6 or 8.

4. A method according to claim 1, wherein the detected activity is binding of the BLC and BLR1 polypeptides.

5. A method according to claim 4, wherein the BLC polypeptide is detectably labeled.

6. A method according to claim 4, wherein the BLC polypeptide has the amino acid sequence of SEQ ID NO: 4 and the BLR1 polypeptide has the amino acid sequence of SEQ ID NO: 8.

7. A method according to claim 1, wherein the detected activity is $Ca^{2+}$ mobilization.

8. A method according to claim 7, wherein the cell is a HEK-293 cell.

9. A method according to claim 7, wherein the BLC polypeptide has the amino acid sequence of SEQ ID NO: 4 and the BLR1 polypeptide has the amino acid sequence of SEQ ID NO: 8.

10. A method according to claim 1, wherein the detected activity is chemotaxis.

11. A method according to claim 10, wherein the cell is a Jurkat cell.

12. A method according to claim 10, wherein the cell is a B lymphocyte.

13. A method according to claim 10, wherein the BLC polypeptide has the amino acid sequence of SEQ ID NO: 4 and the BLR1 polypeptide has the amino acid sequence of SEQ ID NO: 8.

14. A method for identifying agents that modulate the interaction of a B Lymphocyte Chemoattractant (BLC) polypeptide and a Burkitt's Lymphoma Receptor-1 (BLR1) polypeptide, comprising:

providing a membrane preparation comprising a BLR1 polypeptide, wherein the BLR1 polypeptide has the amino acid sequence of a protein encoded by DNA that specifically hybridizes under stringent conditions to a probe complementary to the full length of SEQ ID NO: 5 or 7;

contacting the membrane preparation with a BLC polypeptide and a candidate modulatory agent, wherein the BLC polypeptide has the amino acid sequence of a protein encoded by DNA that specifically hybridizes under stringent conditions to a probe complementary to the full length of SEQ ID NO: 1 or 3;

detecting the binding of the BLC polypeptide to the BLR1 polypeptide, wherein an identical BLC polypeptide binds to the BLR1 polypeptide with a detectable reference affinity when contacted with an identical membrane preparation under the same conditions in the absence of the candidate agent; and comparing the binding detected in the presence of the candidate agent to said reference affinity, wherein an increase or decrease in said binding relative to said reference affinity indicates that the agent modulates the interaction of the BLC and BLR1 polypeptides;

wherein a chemokine having the same amino acid sequence as the BLC polypeptide is capable of
 (a) inducing $Ca^{2+}$ mobilization in HEK-293 cells expressing a reference chemokine receptor, or
 (b) inducing a chemotactic response in Jurkat cells expressing a reference chemokine receptor, the reference chemokine receptor having the amino acid sequence set forth in SEQ ID NO: 6 or 8;

and wherein a reference BLC chemokine having the amino acid sequence set forth in SEQ ID NO: 2 or 4 is capable of
 (a) inducing $Ca^{2+}$ mobilization in HEK-293 cells expressing a chemokine receptor, or
 (b) inducing a chemotactic response in Jurkat cells expressing a chemokine receptor, the chemokine receptor having the same amino acid sequence as the BLR1 polypeptide.

15. A method according to claim 14, wherein the BLC polypeptide has the amino acid sequence of SEQ ID NO: 2, SEQ ID NO: 4, or a fragment of SEQ ID NO: 2 or 4.

16. A method according to claim 14, wherein the BLR1 polypeptide has the amino acid sequence of SEQ ID NO: 6, SEQ ID NO: 8, or a fragment of SEQ ID NO: 6 or 8.

17. A method according to claim 14, wherein the BLC polypeptide is detectably labeled.

18. A method according to claim 14, wherein the BLC polypeptide has the amino acid sequence of SEQ ID NO: 4 and the BLR1 polypeptide has the amino acid sequence of SEQ ID NO: 8.

19. A method for assessing the functional properties or a B Lymphocyte Chemoattractant (BLC) variant, comprising:

providing a cell expressing a BLR1 polypeptide, wherein the BLR1 polypeptide has the amino acid sequence of a protein encoded by DNA that specifically hybridizes under stringent conditions to a probe complementary to the full length of SEQ ID NO: 5 or 7;

contacting the cell with a BLC variant polypeptide having the amino acid sequence of a protein encoded by DNA that specifically hybridizes under stringent conditions to a probe complementary to the full length of SEQ ID NO: 1 or 3; and detecting an activity selected from the group consisting of binding of the BLC variant polypeptide to the BLP1 polypeptide, $Ca^{2+}$ mobilization, and chemotaxis;

wherein a reference BLC chemokine having the amino acid sequence set forth in SEQ ID NO: 2 or 4 is capable of
  (a) inducing $Ca^{2+}$ mobilization in HEK-293 cells expressing a chemokine receptor, or
  (b) inducing a chemotactic response in Jurkat cells expressing a chemokine receptor, the chemokine receptor having the same amino acid sequence as the BLR1 polypeptide.

20. A method according to claim 19, wherein the BLC variant polypeptide has the amino acid sequence of a fragment of SEQ ID NO: 2 or 4.

21. A method according to claim 19, wherein the BLR1 polypeptide has the amino acid sequence of SEQ ID NO: 6, SEQ ID NO: 8, or a fragment of SEQ ID NO: 6 or 8.

22. A method according to claim 21, wherein the BLR1 polypeptdde has the amino acid sequence of SEQ ID NO: 8.

23. A method according to claim 19, wherein the detected activity is binding of the BLC variant and BLR1 polypeptides.

24. A method according to claim 23, wherein the BLC variant polypeptide is detectably labeled.

25. A method according to claim 19, wherein the detected activity is $Ca^{2+}$ mobilization.

26. A method according to claim 25, wherein the cell is a HEK-293 cell.

27. A method according to claim 25, wherein the BLR1 polypepide has the amino acid sequence of SEQ ID NO: 8.

28. A method according to claim 19, wherein the detected activity is chemotaxis.

29. A method according to claim 28, wherein the cell is a Jurkat cell.

30. A method according to claim 28, wherein the cell is a B lymphocyte.

31. A method according to claim 28, wherein the BLR1 polypeptide has the amino acid sequence of SEQ ID NO: 8.

32. A method for assessing the functional properties of a Burkitu's Lymphoma Receptor-1 (BLR1) variant, comprising:

providing a cell expressing a BLR1 variant polypeptide, wherein the BLR1 polypeptide has the amino acid sequence of a protein encoded by DNA that specifically hybridizes under stringent conditions to a probe complementary to the full length of SEQ ID NO: 5 or 7;

contacting the cell with a BLC polypeptide having the amino acid sequence of a protein encoded by DNA that specifically hybridizes under stringent conditions to a probe complementary to the full length of SEQ ID NO: 1 or 3; and detecting an activity selected from the group consisting of binding of the BLC polypeptide to the BLR1 variant polypeptide, $Ca^{2+}$ mobilization, and chemotaxis;

wherein a chemokine having the same amino acid sequence as the BLC polypeptide is capable of
  (a) inducing $Ca^{2+}$ mobilization in HEK-293 cells expressing a reference chemokine receptor, or
  (b) inducing a chemotactic response in Jurkat cells expressing a reference chemokine receptor, the reference chemokine receptor having the amino acid sequence set forth in SEQ ID NO: 6 or 8.

33. A method according to claim 32, wherein the BLC polypeptide has the amino acid sequence of SEQ ID NO: 2, SEQ ID NO: 4, or a fragment of SEQ ID NO: 2 or 4.

* * * * *